(12) United States Patent
Hashimoto et al.

(10) Patent No.: US 8,092,720 B2
(45) Date of Patent: Jan. 10, 2012

(54) POLYMER-SUPPORTED METAL COMPLEX CATALYST

(75) Inventors: Shunichi Hashimoto, Sapporo (JP); Masahiro Anada, Sapporo (JP)

(73) Assignee: National University Corporation Hokkaido University, Hokkaido (JP)

( * ) Notice: Subject to any disclaimer, the term of this patent is extended or adjusted under 35 U.S.C. 154(b) by 63 days.

(21) Appl. No.: 12/309,660

(22) PCT Filed: Jun. 20, 2007

(86) PCT No.: PCT/JP2007/062379
§ 371 (c)(1),
(2), (4) Date: Jan. 26, 2009

(87) PCT Pub. No.: WO2008/013009
PCT Pub. Date: Jan. 31, 2008

(65) Prior Publication Data
US 2009/0227743 A1   Sep. 10, 2009

(30) Foreign Application Priority Data
Jul. 25, 2006   (JP) .................................. 2006-201726

(51) Int. Cl.
*H01B 1/20* (2006.01)
*B01J 31/12* (2006.01)
(52) U.S. Cl. ................ 252/519.2; 252/519.21; 525/360; 560/122; 560/102; 549/468; 502/161; 502/166
(58) Field of Classification Search ............... 252/519.2, 252/519.21; 525/360; 560/122, 102; 549/468; 502/161, 166
See application file for complete search history.

(56) References Cited

U.S. PATENT DOCUMENTS

| | | | | |
|---|---|---|---|---|
| 4,725,568 A * | 2/1988 | Parker et al. | ................... | 502/159 |
| 4,983,564 A * | 1/1991 | Callahan et al. | ............... | 502/116 |
| 5,789,333 A * | 8/1998 | Angelici et al. | ............... | 502/113 |
| 5,942,461 A * | 8/1999 | Brown et al. | ................... | 502/154 |
| 6,214,878 B1 * | 4/2001 | Bernardon et al. | ........... | 514/569 |
| 6,294,495 B1 * | 9/2001 | Matsunaga | ................... | 502/103 |
| 6,372,682 B2 * | 4/2002 | Ponasik et al. | ................ | 502/117 |
| 6,420,492 B1 * | 7/2002 | Kusakabe et al. | ............. | 525/370 |
| 6,667,369 B2 * | 12/2003 | Kusakabe et al. | ............. | 525/342 |
| 6,878,838 B2 * | 4/2005 | Lin et al. | .......................... | 556/14 |
| 6,927,261 B2 * | 8/2005 | Shih | .................................. | 526/89 |
| 6,946,560 B2 * | 9/2005 | Buchwald et al. | ............. | 546/339 |
| 6,984,604 B2 * | 1/2006 | Cobb et al. | ..................... | 502/159 |
| 7,026,266 B2 * | 4/2006 | Chaudhari et al. | ............ | 502/155 |
| 7,026,498 B2 * | 4/2006 | Buchwald et al. | ............. | 556/413 |
| 7,049,473 B2 * | 5/2006 | Mackewitz et al. | ........... | 568/454 |
| 7,060,840 B2 * | 6/2006 | Deng et al. | ................. | 548/322.5 |
| 2002/0111264 A1 * | 8/2002 | Agapiou et al. | ............... | 502/150 |
| 2004/0220049 A1 * | 11/2004 | Hems et al. | .................... | 502/150 |
| 2007/0125981 A1 * | 6/2007 | Roberts et al. | ........... | 252/299.01 |

FOREIGN PATENT DOCUMENTS

| | | |
|---|---|---|
| JP | 2003-236388 | 8/2003 |
| JP | 2003-326172 | 11/2003 |
| JP | 2004161861 | 6/2004 |
| WO | WO 2003/045552 | 6/2003 |
| WO | WO 2008/013009 | 1/2008 |

OTHER PUBLICATIONS

CAS Reg. No. 1004269-40-2, Feb. 18, 2008.*
Tsutsui, H., et al., "Practical Synthesis of Dirhodium(II) Tetrakis[N-phthaloyl-(S)-tert-leucinate]", Chem. Pharm. Bull., 53(10), 1366-1368 (2005).*
Yamawaki, M., et al., "Dirhodium(II) tetrakis [N-tetrachlorophthaloyl-(S)-tert-leucinate]: a new chiral Rh(II) catalyst for enantioselective amidation of C-H bonds", Tetrahedron Letters, 43, 9561-9564 (2002).*
Andersen et al., "Preparation and Catalytic Properties of Resin Bound Binuclear Rhodium Tetracarboxylate Complexes," Tetrahedron Letters, Elsevier, Amsterdam, vol. 39, No. 42, pp. 7815-7818 (Oct. 15, 1998).
Biffis et al., "A green protocol for the silylation of alcohols using bonded fluorous phase catalysis," Green Chem., vol. 5, pp. 170-173 (2003).
Davies et al., "Asymmetric Intermolecular C—H Activation, Using Immobilized Dirhodium Tetrakis((S)-N-(dodecylbenzenesulfonyl)-prolinate) as a Recoverable Catalyst," Org. Lett., vol. 5, pp. 479-482 (2003).
Davies, "Catalytic Enantioselective CH Activation by Means of Metal-carbenoid-induced CH insertion," Chem. Rev. vol. 103, pp. 2861-2903 (2003).
Davies et al., "Simple Strategy for the Immobilization of Dirhodium Tetraprolinate Catalysts Using a Pyridine-Linked Solid Support," J. Am. Chem. Soc., vol. 126, pp. 4271-4280 (2004).
Doyle et al., "Enantioselective Metal Carbene Transformations with Polyethylene-Bound Soluble Recoverable Dirhodium(II) 2-Pyrrolidone-5(S)-carboxylates," J. Org. Chem., vol. 57, pp. 6103-6105 (1992).
Doyle et al., "Recent Advances in Asymmetric Catalytic Metal Carbene Tranformations," Chem. Rev., vol. 98, pp. 911-935 (1998).
McNamara et al., "Recoverable Catalysts and Reagents Using Recyclable Polystyrene-Based Supports," Chem. Rev., vol. 102, pp. 3275-3300 (2002).

(Continued)

*Primary Examiner* — Douglas McGinty
(74) *Attorney, Agent, or Firm* — Jenkins, Wilson, Taylor & Hunt, P.A.

(57) ABSTRACT

Polymer supported metal complex catalysts and methods of their preparation and use are described. The polymer supported metal complex catalysts can be obtained via ligand exchange reactions between polymer ligands and a metal complex having catalytic activity. For example, a polymer supported rhodium (II) complex catalyst can be prepared via ligand exchange reaction between an insoluble polymer and a rhodium (II) carboxylate complex, wherein the insoluble polymer is prepared by a copolymerization reaction of (i) a styrene derivative with a substituted carboxylic acid, (ii) a styrene, and (iii) a linear alkane with both ends substituted by vinylbenzyloxy groups. The polymer supported catalysts can be used to catalyze asymmetric carbene reactions such as C—H insertion reactions and the like with high catalytic activity, chemical selectivity, diastereoselectivity, and enantioselectivity.

7 Claims, 2 Drawing Sheets

OTHER PUBLICATIONS

Merlic et al., "Selectivity in Rhodium(II) Catalyzed Reactions of Diazo Compounds: Effects of Catalyst Electrophilicit, Diazo Substitution, and Substrate Substitution. From Chemoselectivity," Synthesis, pp. 1137-1156 (2003).

Minami et al., "Highly Enantio- and Diastereoselective Construction of 1,2-Disubstituted Cyclopentane Compounds by Dirhodium(II) Tetrakis[N-phthaloyl-(S)-tert-leucinate]-Catalyzed CH Insertion Reactions of α-Diazo Esters," Adv. Synth. Catal., vol. 347, No. 11-13, pp. 1483-1487 (Oct. 2005).

Spanka et al., "Preparation of New Microgel Polymers and Their Application as Supports in Organic Synthesis," J. Org. Chem., vol. 67, No. 9, pp. 3045-3050 (2002).

Supplementary European Search Report corresponding to European Application No. 07767218.6-2104 / 2045014 PCT/JP2007062379 dated Aug. 3, 2009.

International Preliminary Report on Patentability corresponding to International Application No. PCT/JP2007/062379 dated Feb. 19, 2008.

International Search Report corresponding to International Patent Application No. PCT/JP2007/062379 dated Sep. 18, 2007.

* cited by examiner

[FIG. 1]
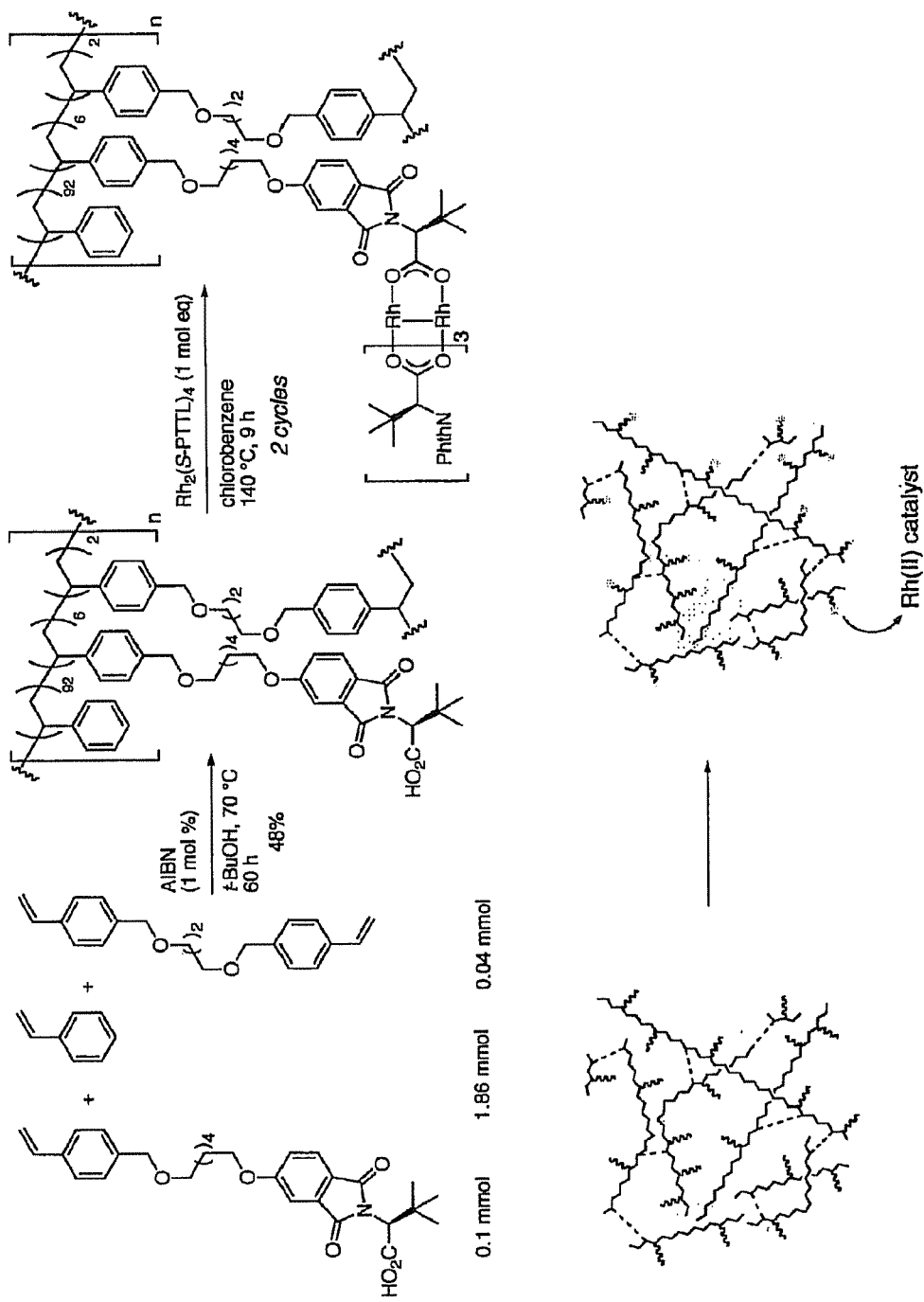

[FIG. 2]
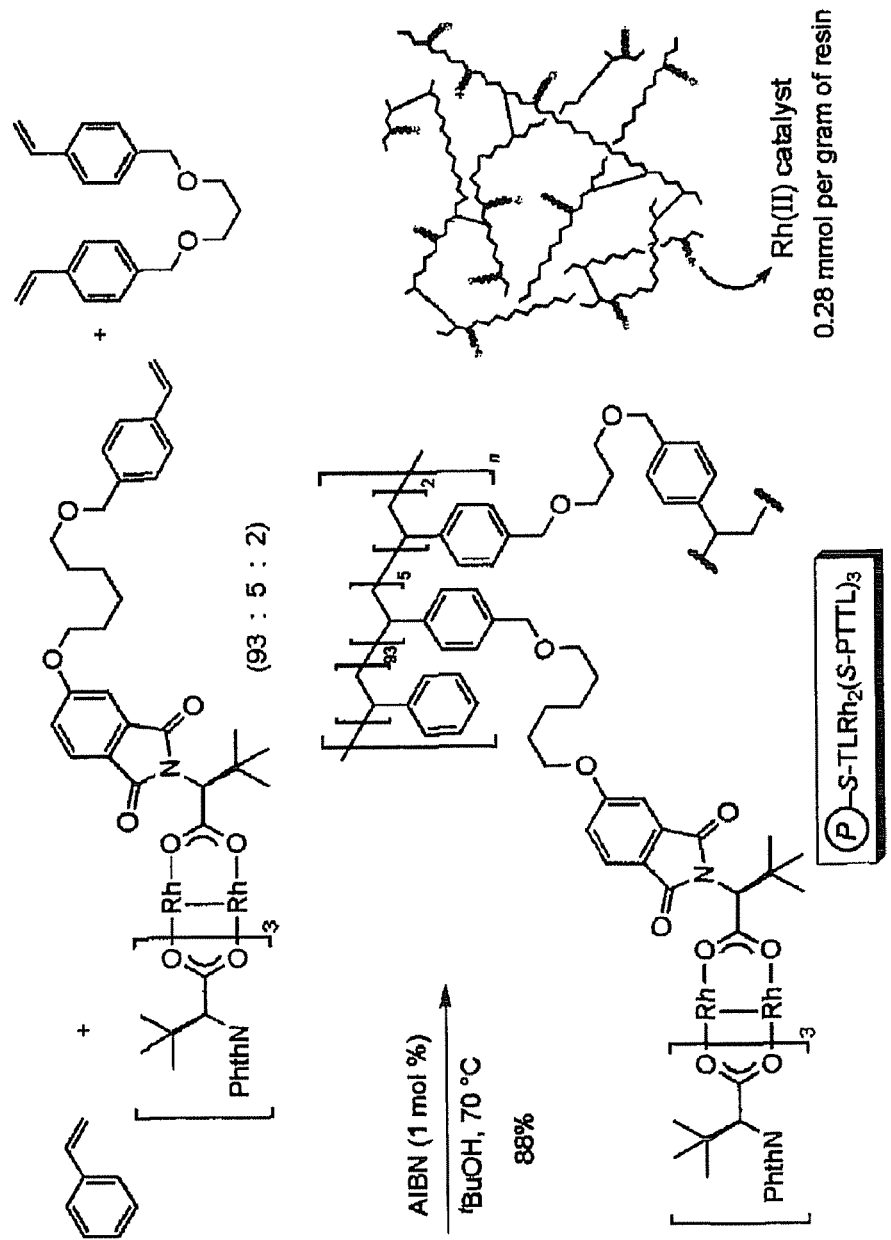

POLYMER-SUPPORTED METAL COMPLEX CATALYST

FIELD OF THE INVENTION

The present invention relates to a polymer-supported rhodium (II) catalyst and its application, which includes addition reaction to carbon-carbon multiple bond in α-diazocarbonyl compounds, insertion reaction to C—H and X—H (X=N, O, S, Se, Si and the like) bonds, or rearrangement and additional cyclization reaction thereof. The present invention contributes to an atom economy required in the field including organic synthesis and in other fields.

BACKGROUND OF THE INVENTION

Rhodium (II) complex represented by $Rh_2(OAc)_4$ easily decomposes α-diazocarbonyl compound under much milder condition than transition metals such as cupper and complex of transition metal, to generate rhodium (II) carbene intermediate, although its structure has not been proved.

Carbene carbon in rhodium (II) carbene intermediate shows extremely high electrophilicity and there are various reactions based on the intermediate. The reaction includes, for example, addition to carbon-carbon multiple bond, insertion to C—H and X—H (X=N, O, S, Se, Si and the like) bonds or rearrangement and additional cyclization reaction triggered by ylide formation, etc. All of the above reactions are catalytic reactions and they are important reactions in synthetic chemistry because of simultaneous formation of carbon-carbon bond formation and generation of asymmetric carbon (Reference 1).

$Rh_2(OAc)_4$ may easily replace acetato, a bridging ligand, with various carboxylato and amidato by a ligand exchange reaction, and may synthesize rhodium(II) complexes with various characteristics. For example, Doyle et al. developed asymmetric amidato complex $Rh_2(5S\text{-MEPY})_4$, $Rh_2(4S\text{-MPPIM})_4$ and the like with fixed asymmetric space (Reference 2). The present complex has high enantio selectivity in intramolecular C—H insertion reaction of α-diazoacetato or α-diazoacetamide and intramolecular cyclopropane formation reaction thereof. McKervey, Davies et al. developed rhodium (II) carboxylato complex, wherein allenesulfonylprolinato was incorporated in bridging ligand. Particularly, $Rh_2(S\text{-DOSP})_4$ developed by Davies et al. accomplished extremely high enantio selectivity in intermolecular C—H insertion reaction of phenyldiazoacetato or vinyldiazoacetato and intermolecular cyclopropane formation reaction thereof performed in hexane (Reference 3).

The present inventors developed rhodium (II) carboxylato complex integrated with optically active N-phthaloylamino acid as a bridging ligand and reported intramolecular asymmetric C—H insertion reaction and asymmetric additional cyclization and rearrangement reaction via ylide formation by the use of various α-diazocarbonyl compounds as substrates (Reference 4).

Asymmetric catalytic reaction by homogeneous transition metal complex has often difficulties in separation and purification between catalysts and products after the reaction. Particularly, the field including medications, cosmetics and foods necessitate to remove strictly heavy metal from products. Furthermore, there are economical problems in applying to large-scale synthesis, since the complex needs expensive ligands and metal. Consequently, development of removal method of metal complex or recoverable and reusable catalysts has been actively performed (Reference 5).

One of the solution concerning removal, recovery and reuse of rhodium (II) complex includes supporting of rhodium (II) complex immobilized in insoluble solid-phase carriers. Use of solid-phase rhodium (II) complex enables theoretically easy separation from products, recovery and reuse of expensive rhodium complex, and prevention of metal from releasing. For example, Doyle et al. developed rhodium (II) amidato complex $Rh_2(S\text{-PYCA})_4$, whose bridging ligand is pyrrolidinone-5(S)-caroxylato incorporated with soluble polyethylene. They are successful in reusing the complex several times maintaining good asymmetric yield in intramolecular asymmetric C—H insertion reaction of α-diazoacetato (Reference 6). Moreover, Davies et al. paid attention to the property of binuclear rhodium (II) complex, whose axial position is occupied by various Lewis basic axial ligands, and proposed a supporting method, wherein $Rh_2(S\text{-DOSP})_4$ and various rhodium (II) complexes are coordinated with pyridines on solid-phase. In intermolecular asymmetric C—H insertion reaction of phenyldiazoacetato, they found that solidified $Rh_2(S\text{-DOSP})_4$ catalyst showed catalytic activity and asymmetry discriminative ability similar to those by $Rh_2(S\text{-DOSP})_4$ alone (Reference 7). While, Biffis et al. developed a catalyst, wherein rhodium (II) perfluorocarboxylato complex is supported by silica gel incorporated with perfluoroalkyl chains, and accomplished recovery and reuse of the catalysts in silanization reaction of alcohols (Reference 8).

Reference 1: Synthesis, 2003, 1137-1156.
Reference 2: Chem. Rev. 1998, 98, 911-935.
Reference 3: Chem. Rev. 2003, 103, 2861-2903.
Reference 4: Adv. Synth. Catal. 2005, 347, 1483-1487.
Reference 5: Chem. Rev. 2002, 102, 3275-3300.
Reference 6: J. Org. Chem. 1992, 57, 6103-6105.
Reference 7: Org. Lett. 2003, 5, 479-482.
Reference 8: Green Chem. 2003, 5, 170-173.

Problems to be Solved by the Invention

Much attention has been paid recently to the field of development of solid-phase rhodium (II) complex, which enables recovery and reuse of the catalyst. Although recovery and reuse of a rhodium complex is easy when using $Rh_2(S\text{-PYCA})_4$ as reported by Doyle et al., the catalyst based on rhodium (II) amidato complex with low catalytic activity has much lower catalytic activity and asymmetry discriminative ability than the master block catalyst due to the solid-phase-support. Additionally, the method of Davies and Biffs et al. cannot prevent metal complex from releasing, and catalytic activity thereof decreases with repeating use, because supporting of rhodium (II) complex in insoluble polymers is not by covalent bonding. Therefore there is a room for improving for all the reported cases. Particularly, the reaction using these catalysts is difficult at low temperature.

The present inventors investigated the development of solid-phase catalyst, wherein insoluble polymer-supported rhodium (II) carboxylato complex incorporated optically active N-phthaloylamino acid as a bridging ligand, and shows high catalytic activity and asymmetry discrimination ability in many diazo decomposition reactions

Means to Solve the Problems

As the result, the present inventors developed a method for preparing a novel insoluble polymer-supported rhodium (II) complex, which comprises a ligand exchange reaction between an insoluble polymer and a rhodium (II) carboxylato complex, wherein the insoluble polymer was prepared by a copolymerization reaction of (i) a styrene derivative with substituted carboxylic acid, (ii) a stylene, and (iii) a linear alkane with both ends substituted by vinylbenzyloxy groups, and accomplished the present invention.

Namely, the present invention is a polymer-supported metal complex catalyst represented by the following chemical formula 1

[chemical formula 1]

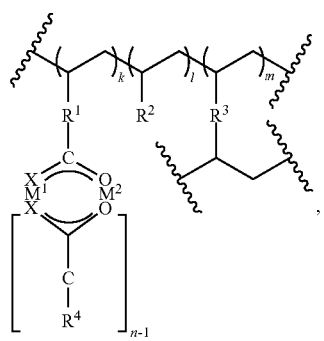

wherein $M^1$ and $M^2$, which may be identical to or different from the others, are selected from a group consisting of rhodium, palladium, ruthenium, rhenium, iron, nickel, cupper, platinum, bismuth, cobalt, chrome, molybdenum, and tungsten; and X is an oxygen atom, a sulfur atom or a group represented by $=NR^5$, wherein $R^5$ represents a hydrogen atom or an alkyl group, and $R^4$ is an alkyl group, an aryl group, an aralkyl group, an alkyloxy group or an alkylamino group, which may have substituents; k is 1 to 15% and m is more than 0 and equal to or less than 99% based on k+l+m and l is the remainder; and n is an integer between 2 and 4, which is determined by the valences of $M^1$ and $M^2$; and $R^1$ to $R^3$ are defined below, wherein the polymer is a crosslinked polymer which is prepared by a copolymerization of (1) a coordinating monomer represented by the chemical formula 2:

[chemical formula 2]

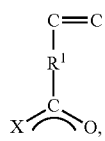

wherein $R^1$ is a divalent hydrocarbon group, which may contain heteroatoms; and X is defined as above; and other carbons in the vinyl group may have substituents, (2) a hydrophobic monomer represented by the chemical formula 3,

[chemical formula 3]

wherein $R^2$ is an aromatic group and other carbons in the vinyl group may have substituents, and (3) a polymeric monomer represented by the chemical formula 4

[chemical formula 4]

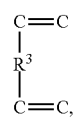

wherein $R^3$ is a divalent hydrocarbon group, which may contain heteroatoms; and other carbons in the vinyl group may have substituents, wherein the polymer-supported metal complex catalyst is formed by a ligand exchange reaction between the crosslinked polymer and a complex represented by the following chemical formula 5

$$(R^4CXO)_n M^1 M^2,$$ [chemical formula 5]

wherein $R^4$, X, n, $M^1$ and $M^2$ are defined as above.

BRIEF DESCRIPTION OF THE DRAWINGS

FIG. 1 shows a method for preparing the polymer supported metal complex catalyst in Example 1.

FIG. 2 shows an another method for preparing the polymer supported metal complex catalyst in Example 2.

DETAILED DESCRIPTION OF THE INVENTION

The polymer-supported metal complex catalyst of the present invention can be prepared by the following procedures.

In the beginning, polymer parts functioning as ligands are synthesized. The polymer is obtained by the copolymerization of the following monomers.

(1) a coordinating monomer having the following general formula (chemical formula 2)

[chemical formula 2]

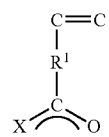

wherein $R^1$ is a divalent hydrocarbon group, which may contain heteroatoms, preferably alkyl-2-(4'-alkyloxyphthalimidomethyl) group;

X is an oxygen atom, a sulfur atom or a group represented by $=NR^5$, preferably oxygen, wherein $R^5$ is a hydrogen atom or an alkyl group, preferably a hydrogen atom.

The carbons in the vinyl group may have substituents, wherein the substituents include alkyl group such as methyl group and alkyloxy groups at ca position.

The coordinating monomer is, for example, N-4-[6-(4-vinylbenzyloxy) hexyl]oxyphthaloyl-(S)-tert-leucine, N-4-[6-(4-vinylbenzyloxy) hexyl]oxyphthaloyl-(S)-phenylalanine or 6-hexenoic acid and the like.

(2) a hydrophobic monomer having the following general formulae (chemical formula 3):

[chemical formula 3]

wherein R² is an aromatic group, preferably phenyl, α- or β-naphthyl group.

The carbons in the vinyl group may have substituents. Such substituent includes a methyl group, an ethyl group, a phenyl group, a methoxyl group and the like.

The hydrophobic monomer is, for example, styrene, 4-methylstyrene, α-methylstyrene, β-methylstyrene, stilbene or vinylnaphthalene and the like.

(3) a polymeric monomer having the following general formulae (chemical formula 4):

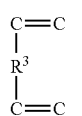

[chemical formula 4]

wherein R³ is a divalent hydrocarbon group, which may contain heteroatoms, preferably 4,4'-(1,3-propyrene-1,3-dioxymethyl)phenyl group.

The carbons in the vinyl group may have substituents. Such substituents include methyl, ethyl, phenyl groups and the like.

The polymeric monomer is preferably a monomer represented by the following formulae (chemical formula 6):

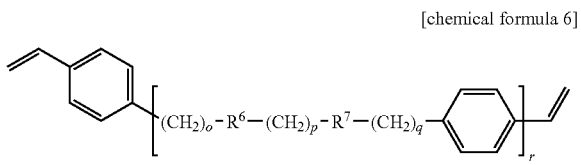

[chemical formula 6]

wherein R⁶ and R⁷ are independently —O—, —S—, —NR⁸— or —PR⁹—, preferably —O— or —NR⁸—, wherein R⁸ and R⁹ are independently a hydrogen atom, an alkyl group, an aryl group or an acyl group, preferably an acetyl group or a phenyl group. The alkyl group is preferably an alkyl group with 1-3 carbon atoms, and the aryl group is preferably a phenyl group.

o is an integer between 0 and 4, preferably 0 or 1; p is an integer between 1 and 12, preferably an integer between 3 and 8, more preferably an integer between 4 and 6; q is an integer between 0 and 4, preferably 0 or 1; and r is an integer between 0 and 20, preferably an integer 1 or 2.

The polymeric monomers are exemplified by 1,3-bis (4-vinylbenzyloxy) propane, 1,4-bis(4-vinylbenzyloxy) butane or 1,4-divinylbenzene.

The molar ratio (k:l:m) of coordinating monomer: hydrophobic monomer: polymeric monomer in a synthesized polymer are determined in a way that k is 1 to 15% and m is more than 0 and equal to or less than 99% relative to k+l+m and l is the remainder.

The solvents usable to the copolymerization reaction include alcohol solvents such as tert-butyl alcohol, isopropyl alcohol, ethanol and the like or hydrocarbon solvents such as toluene and the like. Tert-butyl alcohol is preferably used to obtain excellent results.

The concentration range between 20 and 50% by weight is used, but a high concentration range as much as possible is preferable. Polymerization initiator used includes azobisisobutyronitrile, benzoyl peroxide, tert-butylhydroperoxide, hydrogen peroxide-ferrous (II) salt or hydrogen peroxide-triethylaluminum and the like. The reaction temperature is selected from the range between 0° C. and reflux temperature of a solvent, and preferably around at 70° C.

The reaction time depends on the reaction temperature and the composition of monomers, and is selected suitably from the time range between 1 and 96 hr.

When N-4-[6-(4-vinylbenzyloxy)hexyl]oxyphthaloyl-(S)-tert-leucine, styrene and 1,3-bis(4-vinylbenzyl oxy) propane were copolymerized, functional group (carboxyl group in this case), which will become ligands, can be introduced in the inside of polymers and also produced polymers show high motility similar to micro gels, by suitable control of solvent, reaction temperature and concentrations at the time of polymerization [Spanka, C.; Clapham, B.; Janda, K. D. J. Org. Chem. 2002, 67, 3045-3050]. In other words, when the ratio of N-4-[6-(4-vinylbenzyloxy) hexyl]oxyphthaloyl-(S)-tert-leucine to styrene is 5:93, space and mobility necessary for progress of ligand exchange reaction of rhodium complex in inside of the polymers can be ensured. Furthermore, introduction of cross-linking agent with high degree of freedom as 1,3-bis(4-vinylbenzyloxy) propane enables easy invasion of metal complex to the inside of polymers relative to polymer carriers represented by conventional Merrifield resins because of great swelling of the present insoluble polymers in a solvent, and thus leads to high incorporation rate of metal complexes in the present polymer carriers. Moreover, high swelling ability of the present solid phase-supported catalyst based on mobility and high degree of freedom of long chain linkers substituted for N-phthaloyl-(S)-tert-leucine portion on cross-linking agents and carriers accomplish not only reaction at low temperature, in which conventional solid catalysts cannot be subjected, but also durability to physical abrasion, which enables frequent usage.

Then, the polymer-supported metal complex catalyst of the present invention is formed by ligand exchange between the polymer ligands and metal-containing complex with catalytic activity.

The complex is represented by the following general formula (chemical formula 5):

wherein M¹ and M², which may be identical to or different from the others, are selected from a group consisting of rhodium, palladium, ruthenium, rhenium, iron, nickel, cupper, platinum, bismuth, cobalt, chrome, molybdenum, and tungsten, preferably rhodium, ruthenium, chrome, molybdenum, tungsten or cupper.

X is defined as above.

R⁴ is an alkyl group, an aryl group, an aralkyl group, an alkyloxy group or an alkylamino group, which may have substituents, preferably an alkyl group or aminoalkyl group.

n is an integer between 2 and 4, which is determined by the valences of M¹ and M². For example, when both M¹ and M² are rhodium (II), ruthenium (II) or cupper (II), n is equal to 4.

The complex is preferably $Rh_2(S-PTTL)_4$ or $Rh_2(O_2CCH_3)_4$.

The ligand exchange reaction is performed by heating the solution containing polymers and complex. Since the reaction is equilibrium reaction, solution containing unreacted rhodium (II) complex and isolated ligands is removed after heating for a specified time and remained solid phase-supported catalyst is washed by a solvent. After the above cycle is repeated several times as required, the solvent is removed under reduced pressure.

The solvent used for the present reaction includes hydrocarbon solvents such as chlorobenzene, toluene, xylene and the like, and is preferably chlorobenzene.

The temperature of the reaction is in the range between about 100° C. and boiling point of a solvent.

The reaction time is selected by the extent of reaction for rhodium (II) complex and typically continues for 1 to 9 hr. Generally, the reaction solution is washed once after 9 hr reaction, and then added again with rhodium (II) complex followed by heating. The cycle is repeated 2 to 3 times. About 50% of carboxyl group in the polymers are coordinated to metal complex by the method.

The polymer-supported metal complex catalyst of the present invention may be prepared by the following method.

Namely, it is possible to synthesize the catalyst as the following way. First, ligand exchange is performed by heating (heating at 110 to 130° C. in high boiling point solvents such as chlorobenzene, toluene, xylene and the like) the equimolar mixture of complex and coordinating monomers (linker binding ligands). Then, side chains with suitable length (alkyl group, whose ends must be incorporated with vinylphenyl group, with or without substituents between the groups and the complex) are introduced to phenol hydroxyl groups. After that, hydrophobic monomers (styrene) and polymeric monomers (1,3-bis(4-vinylbenzyloxy) propane) are copolymerized.

In this case, it is possible to copolymerize by vigorously stirring after mixing aqueous solution of gum arabic-salt with chlorobenzene solution containing complex-hydrophobic monomers (styrene)-polymeric monomers (1,3-bis(4-vinylbenzyloxy) propane) in addition to the previous polymerization method. In this case, it is possible to prepare beads catalyst with optional grain size.

According to the above method, the yield in the step for preparing initial rhodium (II) complex is low (unreacted soluble rhodium complex Rh2(S-PTTL)4 is recoverable and reusable in principle). However, the advantage is on the fact that the structure of a metal complex can be checked until immediately before polymerization and that all the carboxyl groups contained in polymers could be coordinated to metal in principle (there are no isolated carboxyl groups in the polymer catalyst).

As the result, it is possible to obtain the polymer-supported metal complex catalyst having the following formula (chemical formula 1):

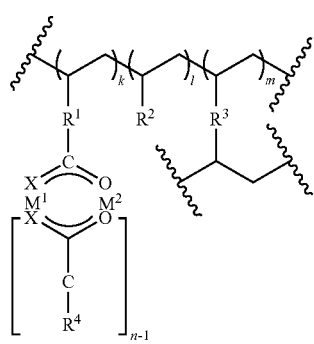

[chemical formula 1]

wherein $R^1$ to $R^4$, X, k, l, m, n, $M^1$, $M^2$ are defined as above.

The polymer-supported metal complex catalyst of the present invention is effective to C—H insertion reaction; cyclopropanization; X—H insertion reaction (X is silica, oxygen, sulfur, or nitrogen); [2,3]-sigmatropy-rearrangement reaction of oxoniumylide, sulfoniumylide or ammoniumylide; [1,2]-rearrangement reaction of oxoniumuylide, sulfoniumylide or ammoniumylide; 1,3-dipolar cycloaddition reaction of carbonylylide, thiocarbonylylide or azomethine ylide; hydrogenation, hydrosilanization, hydroformylation or silylformylation reaction of alkene or alkyne; hydrosilanization of α,β-unsaturated carbonyl compound; Mukouyama-aldol reaction of silylenolether or silylketeneacetal with aldehyde; carbonilene reaction; or Diels-Alder reaction.

These reaction may be performed in halogenated hydrocarbon solvent such as dichloromethane, 1,2-dichloroethane and chloroform; aromatic hydrocarbon solvent such as toluene, benzene, benzotrifluolide, xylene and the like; ether solvent such as ether, tetrahydroflane, methyl-tert-butylether, methylcyclopentylether and the like; ester solvent such as ethylacetate, methylacetate and the like; hydrocarbon solvent such as hexane, pentane and the like; alcohol solvent such as ethanol, methanol and the like; nitrile solvent such as acetonitrile, propionitrile and the like; and nitroalkane solvent such as nitromethane, nitroethane and the like.

The temperature range, in which the present catalysts work, is between −78 and 130° C. and the most suitable temperature may be selected based on the types of reaction to be done and activity of substrates and reactants.

In the reaction of the present catalyst, insoluble catalysts may be removed from reaction mixtures by filtration after stopping the reaction. After the catalysts are filtered off, they are washed with suitable organic solvents for several times, are freed from solvents under reduced pressure and may be reused.

The present invention is illustrated in the following Examples, but these Examples are not intended to limit the scope of the present invention Example 1

First, N-4-benzyloxyphthaloyl-(S)-tert-leucine was synthesized from (S)-tert-leucine. The reaction equation is shown below.

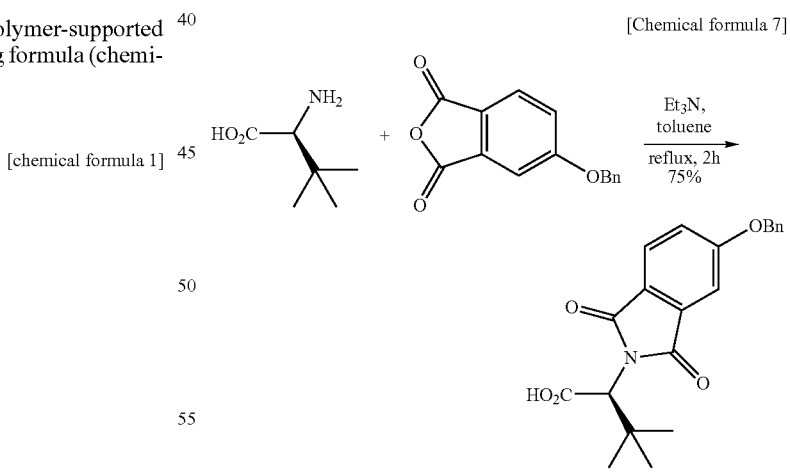

[Chemical formula 7]

In a pear shaped 50 ml flask equipped with an agitator, 1.27 g of 4-benzyloxyphthalic anhydride (5.0 mmoles) and 721 mg of (S)-tert-leucine (5.5 mmoles) were suspended in 15 ml of toluene. Following the addition of 50 mg of triethylamine (0.5 mmole) and attaching a Dean-Stark device, the mixture was heated and refluxed in an oil bath. The disappearance of the starting material and the intermediate was confirmed (two hours), and the reaction solution was allowed to cool to room temperature. Fifteen milliliters of 5% hydrochloric acid was added, and the reaction solution was extracted using ethyl acetate (2×30 ml). The organic layers were combined and washed using saturated aqueous saline solution, dried using anhydrous sodium sulfate, filtered and concentrated to obtain 1.85 g of the crude product in the form of white solids. The solids were recrystallized using hexane-ethyl acetate (3:1, 12 ml), and 1.38 g of N-4-benzyloxyphthaloyl-(S)-tert-leucine (3.75 mmoles, 75%, >99% ee) was obtained in the form of colorless scaly crystals. The analytical data for the product are shown below.

TLC $R_f$ 0.52 (9:1 $CH_2Cl_2$/MeOH); $[\alpha]_D$ –41.0° (c 1.08, $CDCl_3$); IR (KBr) v 3474, 2963, 1956, 1777, 1716, 1616, 1485, 1370, 1278 $cm^{-1}$; $^1$H NMR (270 MHz, $CDCl_3$) δ 1.17 (s, 9H, $C(CH_3)_3$), 4.70 (s, 1H, CH(t-Bu)$CO_2$H), 5.19 (s, 2H, $OCH_2$Ar), 7.24 (m, 1H, ArH), 7.40 (m, 6H, ArH), 7.77 (m, 1H, ArH); $^{13}$C NMR (100.4 MHz, $CDCl_3$) δ; 28.1 ($CH_3$), 35.7 (C), 60.0 (CH), 70.8 (CHO), 109.0 (CH), 121.0 (CH), 123.6 (C), 125.3 (CH), 127.4 (CH), 128.4 (CH), 128.7 (CH), 134.1 (C), 135.3 (C), 163.8 (C), 167.5 (phth C=O), 167.6 (phthC=O), 173.1 (COOH); LRMS (EI) m/z 367 ($M^+$); HRMS (EI) calcd for $C_{21}H_{21}NO_5$: 367.1419. Found: 367.1416. Anal. Calcd for $C_{21}H_{21}NO_5$: C, 68.65; H, 5.76; N, 3.81. Found: C, 68.66; H, 5.76; N, 3.83.

The enantiomeric excess ratio (ee) of the product was determined to be >99% ee according to an HPLC analysis using a chiral column after derivation to the methyl ester using a diazomethane treatment. Analytical conditions: column: Daicel Chiralcel OD-H; eluent: 19:1 hexane/2-propanol; flow: 1.0 mL/min; detection: 254 nm; retention time: 13.1 min (minor enantiomer R), 20.5 min (major enantiomer &.

tion, and the solution was agitated for thirty minutes. The reaction solution was subsequently extracted using 50 ml of ethyl acetate. The organic layer was washed using 20 ml of water followed by 20 ml of saturated aqueous saline solution, dried using anhydrous sodium sulfate, filtered and concentrated to obtain 1.60 g of a crude product. N-4-Benzyloxyphthaloyl-(S)-tert-leucine tert-butyl ester (1.11 g, 2.63 mmoles, 70%, >99% ee) was obtained in the form of a colorless amorphous material using column chromatography purification (50 g silica gel, 10:1 n-hexane/EtOAc). The analytical data for the product are shown below. TLC $R_f$ 0.43 (5:1 hexane/EtOAc); $[\alpha]_D$ –7.80 (c 0.78, EtOH); IR (KBr) v 3474, 2973, 1775, 1717, 1618, 1487, 1373, 1284 $cm^{-1}$; $^1$H NMR (270 MHz, $CDCl_3$) δ 1.17 (s, 9H, $C(CH_3)_3$), 1.40 (s, 9H, $C(CH_3)_3$), 4.55 (s, 1H, CH(t-Bu)$CO_2$t-Bu), 5.19 (s, 2H, $OCH_2$Ar), 7.23 (m, 1H, ArH), 7.42 (m, 6H, ArH) 7.76 (m, 1H, ArH); $^{13}$C NMR (67.8 MHz, $CDCl_3$) δ; 27.9 ($CH_3$), 28.1 ($CH_3$), 35.6 (C), 60.7 (CH), 70.7 ($CH_2$), 81.9 (C), 108.8 (CH), 120.7 (CH), 123.9 (C), 125.1 (CH), 127.5 (CH), 128.5 (CH), 128.8 (CH), 134.3 (C), 135.4 (C), 163.8 (C), 166.9 (C=O), 167.8 (C=O), 167.9 (C=O); LRMS (EI) m/z 423 ($M^+$); HRMS (EI) calcd for $C_{25}H_{29}NO_5$: 423.2045. Found: 423.2050; Anal. Calcd for $C_{25}H_{29}NO_5$: C, 70.90; H, 6.90; N, 3.31. Found: C, 70.83; H, 6.91; N, 3.21.

The enantiomeric excess ratio (ee) of the product was determined to be >99% ee according to an HPLC analysis using a chiral column. Analytical conditions:column: Daicel Chiralcel OD-H; eluent: 19:1 hexane/2-propanol; flow: 1.0 mL/min; detection: 254 nm; retention time: 11.8 min (minor enantiomer R), 18.8 min (major enantiomer S).

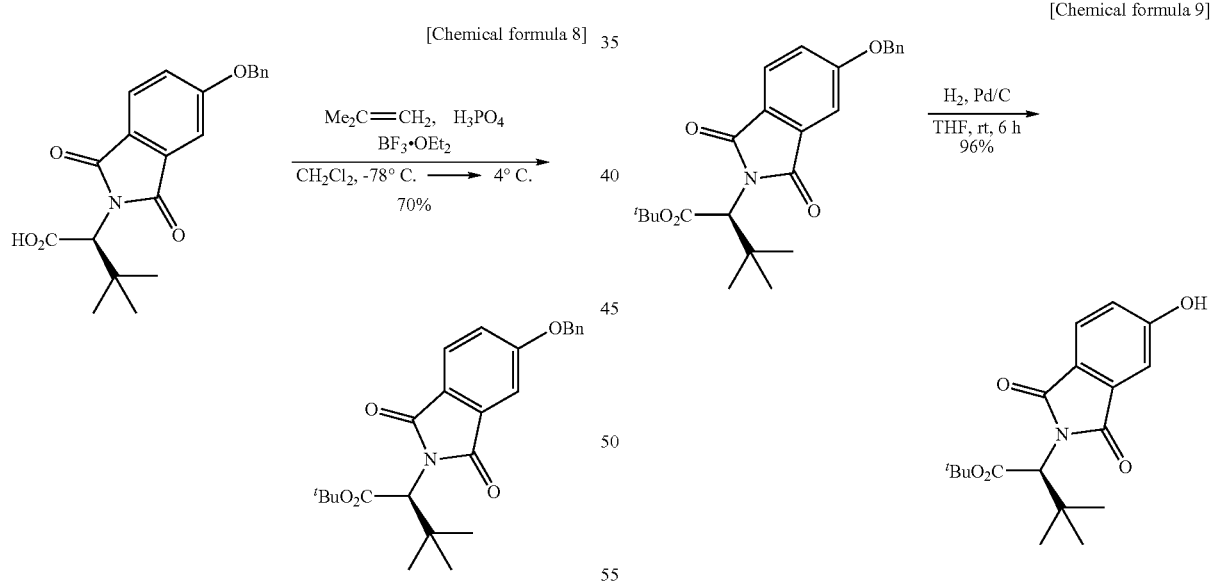

Ten milliliters of a dichloromethane solution of 1.38 g of N-4-benzyloxyphthaloyl-(S)-tert-leucine (3.75 mmoles) was cooled to −78° C., and 6 ml of isobutene, and 1 ml of a dichloromethane solution of phosphoric acid (prepared at the time of use by adding 0.2 ml, 500 mg, of diphosphorous pentoxide to 1.1 ml of 85% phosphoric acid) and 0.3 ml of $BF_3 \cdot OEt_2$ were added consecutively. The reaction solution was agitated for two hours. The reaction solution was subsequently warmed to 4° C. and agitated for additional twenty-four hours. Ten grams of ice chips and 10 ml of aqueous sodium bicarbonate solution were added to the reaction solu- Pd/C (10% Pd/C, 159 mg) was added to 30 ml of a THF solution of N-4-benzyloxyphthaloyl-(S)-tert-leucine tert-butyl ester (1.27 g, 3.0 mmoles), and the reaction mixture was agitated for six hours at room temperature in a hydrogen gas atmosphere. The reaction mixture was filtered, and the residue was washed using 10 ml of THF. N-4-hydroxyphthaloyl-(S)-tert-leucine tert-butyl ester (960 mg, 2.88 mmoles, 96%) was obtained in the form of a colorless amorphous material after the filtrate was concentrated and the residue (1.40 g) was purified using column chromatography (silica gel, 40 g, 3:1 n-hexane/EtOAc). The analytical data for the product are shown below.

TLC R/0.55 (1:1 hexane/AcOEt); [α]$_D$+1.1° (c 0.75, CDCl$_3$); IR (KBr) v 3387, 2975, 1775, 1717, 1615, 1468, 1370, 1261 cm$^{-1}$; $^1$H NMR (270 MHz, CDCl$_3$) δ 1.17 (s, 9H, C(CH$_3$)$_3$), 1.40 (s, 9H, C(CH$_3$)$_3$), 4.57 (s, 1H, CH(t-Bu)CO$_2$ t-Bu), 7.08 (m, 1H, Ar), 7.25 (m, 1H, Ar), 7.67 (m, 1H, Ar); $^{13}$C NMR (100.4 MHz, CDCl$_3$) δ; 28.0 (CH$_3$), 28.4 (CH$_3$), 35.7 (C), 61.2 (CH), 83.0 (C), 110.7 (CH), 120.7 (CH), 122.8 (C), 125.5 (CH), 134.2 (C), 162.0 (C), 167.7 (C), 168.1 (C); LRMS (EI) m/z 334 (MH$^+$); Anal. Calcd for C$_{18}$H$_{23}$NO$_5$: C, 64.85; H, 6.95; N, 4.20. Found: C, 64.94; H, 7.01; N, 4.22.

[Chemical formula 10]

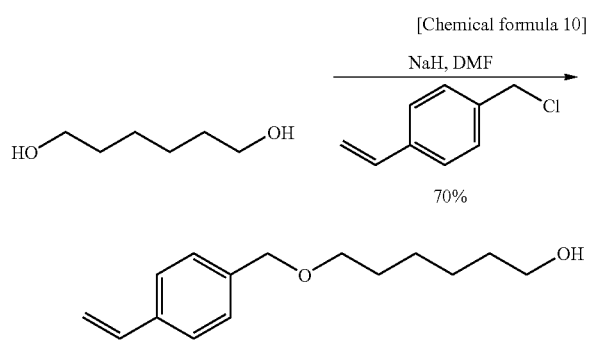

A DMF suspension (5 ml) of sodium hydride (50% in oil, 0.8 g, 16.7 mmoles) was cooled to 0° C., 5 ml of a DMF solution of 1,6-hexamethylene glycol (3.55 g, 30 mmoles) was added dropwise, and the suspension was agitated for fifteen minutes. One milliliter of a DMF solution of 1.53 g of chloromethylstyrene (10 mmoles) was added dropwise over at least five minutes. The reaction solution was subsequently heated to room temperature and was agitated for three hours. The reaction solution was cooled again using an ice bath, was agitated for five minutes after adding 15 ml of water and was extracted using ethyl acetate (2×40 ml). The organic layers were combined and washed sequentially using first 20 ml of water and then 15 ml of saturated aqueous saline solution. The organic layer was dried using anhydrous sodium sulfate, filtered and concentrated to obtain 4.2 g of a crude product. 6-(4-Vinylbenzyloxy) hexanol (1.64 g, 7.0 mmoles, 70%) was obtained in the form of a colorless oily material after using column chromatography (silica gel, 70 g, 9:1→1:1 n-hexane/EtOAc) to purify the material. The analytical data for the product are shown below.

TLC R$_f$0.44 (1:1 hexane/EtOAc); IR (film) v 3403, 2935, 2858, 1630, 1512, 1406, 1364 cm$^{-1}$; $^1$H NMR (270 MHz, CDCl$_3$) δ 1.22 (br, 1H, OH), 1.38 (m, 4H, —CH$_2$—), 1.61 (m, 4H, —CH$_2$—) 3.46 (t, J=5.94 Hz, 2H, OCH$_2$CH$_2$), 3.63 (m, 2H, CH$_2$CH$_2$OH), 4.49 (s, 2H, ArCH$_2$O), 5.23 (d, J=11.2 Hz, 1H, ArCH=CH$_2$), 5.74 (d, J=17.8 Hz, 1H, ArCH=CH$_2$), 6.71 (dd, J=11.2 Hz, 17.8 Hz, 1H, ArCH=CH$_2$), 7.29 (m, 2H, ArH), 7.39 (m, 2H, ArH); $^{13}$C NMR (100.4 MHz, CDCl$_3$) δ 25.6 (CH$_2$), 26.0 (CH$_2$), 29.7 (CH$_2$), 32.7 (CH$_2$), 62.7 (CH$_2$), 70.2 (CH$_2$), 72.5 (CH$_2$), 113.5 (CH$_2$), 126.0 (CH), 127.7 (CH), 136.4 (CH), 136.7 (C), 138.1 (C); LRMS (EI) m/z 234 (M$^+$); HRMS (EI) m/z calcd for C$_{15}$H$_{22}$O$_2$: 234.1620. Found: 234.1618. Anal. Calcd for C$_{15}$H$_{22}$O$_2$: C, 76.88; H, 9.46. Found: C, 76.45; H, 9.42.

[Chemical formula 11]

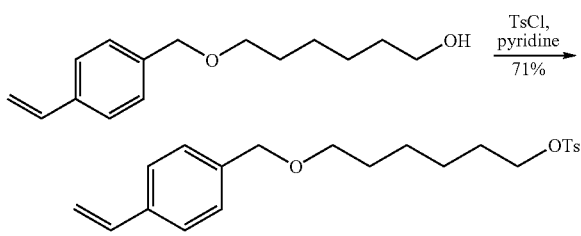

Six milliliters of pyridine was added to dissolve 1.43 g of p-toluene sulfonyl chloride (7.5 mmoles) while cooling with ice. Subsequently, 1.17 g of 6-(4-vinylbenzyloxy) hexanol (5.0 mmoles) was added, and the reaction solution was agitated for three hours at room temperature. The reaction solution was poured into 20 ml of ice water, was vigorously agitated and was subsequently extracted using 50 ml of ethyl acetate. The organic layer was washed sequentially using 20 ml of water and then 20 ml of saturated aqueous saline solution. The organic layer was subsequently dried using anhydrous sodium sulfate, filtered and concentrated to obtain 1.60 g of a crude product. 6-(4-Vinylbenzyloxy) hexyl p-toluene sulfonate (1.38 g, 3.5 mmoles, 71%) was obtained in the form of an oily material after using column chromatography (silica gel, 70 g, 4:1 hexane/EtOAc) to purify the material. The analytical data for the product are shown below.

TLC R$_f$=0.43 (3:1 hexane/AcOEt); IR (film) v 2938, 2861, 1630, 1599, 1512, 1402, 1360, 1177 cm$^{-1}$; $^1$H NMR (270 MHz, CDCl$_3$) δ 1.29-1.34 (m, 4H, —CH$_2$—), 1.53-1.64 (m, 4H, —CH$_2$—), 2.44 (s, 3H, ArCH$_3$), 3.41 (t, J=6.40 Hz, 2H, OCH$_2$CH$_2$), 4.01 (t, J=6.40 Hz, 2H, ArCH$_2$O), 4.46 (s, 2H, CH$_2$CH$_2$OTs), 5.22 (d, J=10.9 Hz, 1H, ArCH=CH$_2$), 5.73 (d, J=16.9 Hz, 1 H, ArCH=CH$_2$), 6.70 (dd, J=10.9 Hz, 16.9 Hz, 1H, ArCH=CHO, 7.20 (m, 2H, ArH), 7.34 (m, 4H, ArH), 7.78 (m, 2H, ArH); $^{13}$C NMR (100.4 MHz, CDCl$_3$) δ 25.2 (CH$_2$), 25.6 (CH$_2$), 28.8 (CH$_2$), 21.5 (CH$_3$), 29.4 (CH$_2$), 70.0 (CH), 70.5 (CH$_2$), 72.5 (CHO), 113.6 (CH$_2$), 126.1 (CH), 127.7 (CH), 129.7 (CH), 133.1 (C), 136.4 (CH), 136.7 (C), 138.1 (C), 144.5 (C); MS (EI) m/z 388 (M$^+$); HRMS (EI) m/z calcd for C$_{22}$H$_{28}$SO$_4$: 388.1708. Found: 388.1708. Anal. Calcd for C$_{22}$H$_{28}$SO$_4$: C, 68.01; H, 7.26; S, 8.25. Found: C, 67.16; H, 7.20; S, 8.19.

[Chemical formula 12]

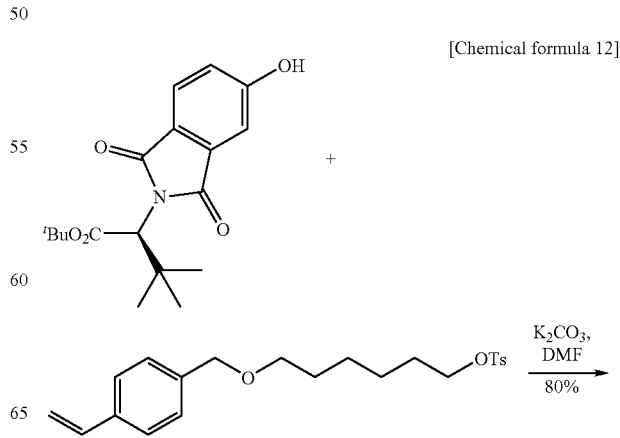

-continued

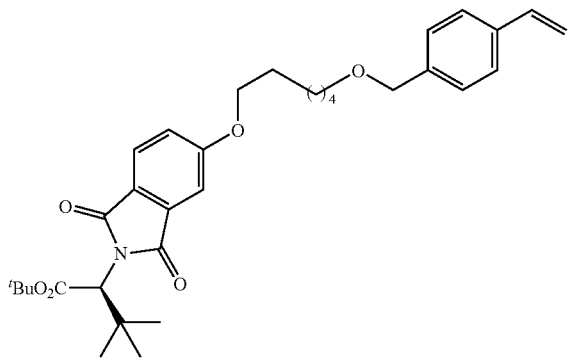

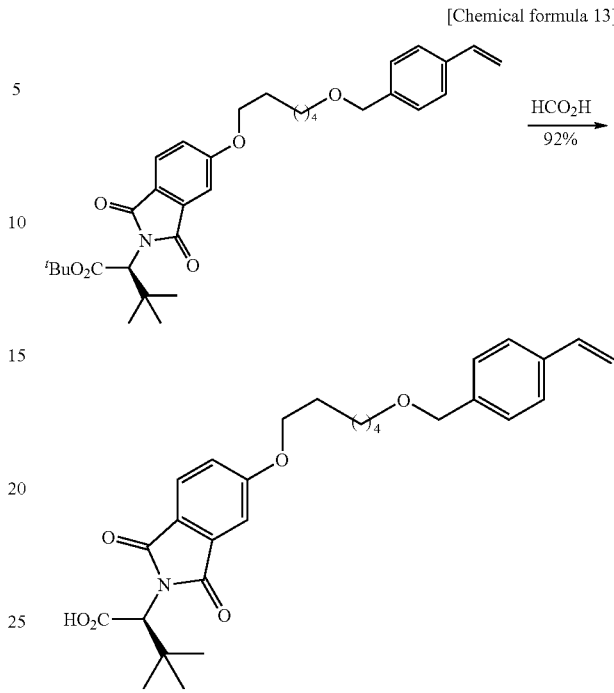

To 5 ml DMF solution of 900 mg of N-4-hydroxyphthaloyl-(S)-tert-leucine tert-butyl ester (2.7 mmoles) was added 746 m g of $K_2CO_3$ (5.4 mmoles). The reaction solution was agitated for five minutes at room temperature (the reaction solution gradually changed to yellow), 1 ml of a DMF solution of 857 mg of 6-(4-vinylbenzyloxy) hexyl toluene sulfonate (2.5 mmoles) was added, and the reaction solution was agitated for three hours at 50° C. Twenty milliliters of water was added to the reaction solution, and ethyl acetate was used to extract it (3×50 ml). The organic layers were combined and washed using 20 ml of saturated aqueous saline solution and dried using anhydrous sodium sulfate. Following filtration and concentration, 1.70 g of the residue was purified using column chromatography (55 g of silica gel, 5:1 n-hexane/$Et_2O$), and 1.07 g of N-4-[6-(4-vinylbenzyloxy)hexyl]oxyphthaloyl-(S)-tert-leucine tert-butyl ester (2.0 mmoles, 80%) was obtained in the form of a colorless oily substance. The analytical data for the product are shown below.

TLC $R_f$ 0.43 (5:1 hexane/EtOAc); $[\alpha]_D$+1.7° (c 1.10, $CHCl_3$); IR (film) v 3474, 2938, 2865, 1775, 1744, 1717, 1618, 1489, 1373 $cm^{-1}$; $^1H$ NMR (270 MHz, $CDCl_3$) δ 1.17 (s, 9H, $C(CH_3)_3$), 1.40 (s, 9H, $C(CH_3)_3$), 1.48 (m, 4H, —C$\underline{H}_2$—), 1.66 (m, 2H, —$CH_2$—), 1.81 (m, 2H, —$CH_2$—), 3.48 (t, J=6.6 Hz, 2H, $OCH_2CH_2$), 4.06 (t, J=6.6 Hz, 2H, $OCH_2CH_2$), 4.49 (s, 2H, $OCH_2Ar$), 4.55 (s, 1H, C$\underline{H}$(t-Bu)$CO_2$t-Bu), 5.23 (d, J=11.2 Hz, 1H, ArCH=$CH_2$), 5.74 (d, J=17.8 Hz, 1H, ArCH=$CH_2$), 6.71 (dd, J=11.2 Hz, 17.8 Hz, ArCH=$CH_2$), 7.15 (m, 1H, ArH), 7.24 (m, 3H, ArH), 7.39 (m, 2H, ArH) 7.74 (m, 1H, ArH); $^{13}$C NMR (67.8 MHz, $CDCl_3$) δ 25.8 ($CH_2$), 25.9 ($CH_2$), 27.9 ($CH_3$), 28.0 ($CH_3$), 28.9 ($CH_2$), 29.7 ($CH_2$), 35.6 (C), 60.8 (CH), 68.8 ($CH_2$), 70.1 ($CH_2$), 72.6 ($CH_2$), 81.8 (C), 108.2 (CH), 113.6 ($CH_2$), 120.3 (CH), 123.3 (C), 125.0 (CH), 126.1 (CH), 127.7 (CH), 134.2 (C), 136.4 (CH), 136.7 (C), 138.1 (C), 164.1 (C), 166.7 (C=O), 167.7 (C=O), 167.8 (C=O); LRMS (EI) m/z 549 ($M^+$); HRMS (EI) calcd for $C_{33}H_{43}NO_6$: 549.3090, found 549.3097; Anal. Calcd for $C_{33}H_{43}NO_6$: C, 72.10; H, 7.88; N, 2.55. Found: C, 70.74; H, 7.89; N, 2.49.

The enantiomeric excess ratio (ee) of the product was determined to be >99% ee according to an HPLC analysis using a chiral column. Analytical conditions: column: Daicel Chiralcel OJ-H; eluent: 19:1 hexane/2-propanol; flow: 1.0 mL/min; detection: 254 nm; retention time: 9.7 min (minor enantiomer R), 16.3 min (major enantiomer S).

[Chemical formula 13]

Nine milliliters of formic acid was added to 1.07 g of N-4-[6-(4-vinylbenzyloxy)hexyl]oxyphthaloyl-(S)-tert-leucine tert-butyl ester (2.0 mmoles, >99% ee), and the mixture was agitated for three hours at room temperature. The reaction solution was concentrated, and 1.10 g of the residue was purified using column chromatography (30 g of silica gel, 2:1 hexane/EtOAc) to obtain 841 mg of N-4-[6-(4-vinylbenzyloxy)hexyl]oxyphthaloyl-(S)-tert-leucine (1.92 mmoles, 92%) in the form of a colorless amorphous material. The analytical data for the product are shown below.

TLC $R_f$ 0.50 (9:1 $CH_2Cl_2$/MeOH); $[\alpha]_D$–14.9° (c 0.56, $CHCl_3$); IR (film) v 2940, 2866, 1775, 1714, 1618, 1489, 1450, 1375 $cm^{-1}$; $^1H$ NMR (270 MHz, $CDCl_3$) δ 1.17 (s, 9H, $C(CH_3)_3$), 1.46 (m, 4H, —$CH_2$—), 1.64 (m, 2H, —$CH_2$—), 1.82 (m, 2H, —$CH_2$—), 3.47 (t, J=6.4 Hz, 2H, $OCH_2CH_2$), 4.05 (t, J=6.4 Hz, 2H, $OCH_2CH_2$), 4.49 (s, 2H, $OCH_2Ar$), 4.69 (s, 1H, CH(t-Bu)$CO_2H$), 5.23 (d, J=10.9 Hz, 1H, ArCH=$CH_2$), 5.74 (d, J=17.5 Hz, 1H, ArCH=$CH_2$), 6.70 (dd, J=10.9 Hz, 17.5 Hz, ArCH=$CH_2$), 7.14 (m, 1H, ArH), 7.29 (m, 3H, ArH), 7.38 (m, 2H, ArH) 7.74 (m, 1H, ArH); $^{13}$C NMR (67.8 MHz, $CDCl_3$) δ 25.8 (CHO, 25.9 ($CH_2$), 28.0 ($CH_3$), 28.9 ($CH_2$), 29.6 ($CH_2$), 35.7 (C), 59.9 (CH), 68.9 ($CH_2$), 70.1 ($CH_2$), 72.6 ($CH_2$), 108.5 (CH), 113.6 ($CH_2$), 120.6 (CH), 123.1 (C), 125.2 (CH), 126.1 (CH), 127.8 (CH), 134.1 (C), 136.4 (CH), 136.8 (C), 138.0 (C), 164.3 (C), 166.7 (C=O), 167.8 (C=O), 172.7 (C=O); MS (EI) m/z 493 ($M^+$); HRMS (EI) m/z calcd for $C_{29}H_{35}NO_6$: 493.2464 found 493.2464.

The enantiomeric excess ratio (ee) of the product was determined to be >99% ee according to an HPLC analysis using a chiral column after derivation of the methyl ester using a diazomethane treatment. Analytical conditions: column: Daicel Chiralcel OJ-H; eluent: 19:1 hexane/2-propanol; flow: 1.0 mL/min; detection: 254 nm; retention time: 11.3 min (minor enantiomer R), 16.9 min (major enantiomer S).

[Chemical formula 14]

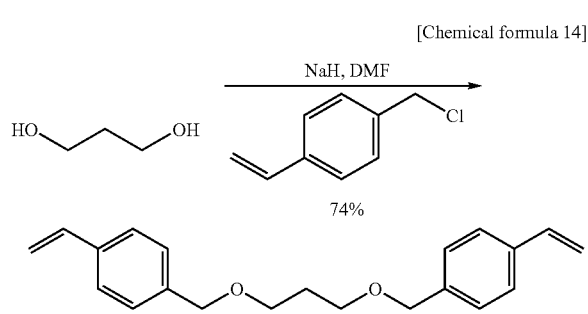

A DMF suspension (5 ml) of sodium hydride (50% in oil, 528 mg, 11 mmoles) was cooled to 0° C., and 3 ml of a DMF solution of 381 mg of 1,3-propane diol (5.0 mmoles) was added dropwise. The reaction mixture was agitated for fifteen minutes, and 1 ml of a DMF solution of 1.53 g of chloromethylstyrene (10 mmoles) was added dropwise over at least five minutes. The reaction solution was heated to room temperature and agitated for three hours. The reaction solution was cooled again using an ice bath, 15 ml of water was added, the solution was agitated for five minutes and was then extracted using ethyl acetate (2×40 ml). The organic layers were combined and washed sequentially using 20 ml of water and 15 ml of a saturated aqueous saline solution, subsequently dried using anhydrous sodium sulfate, filtered and concentrated to obtain 1.6 g of a crude product. The crude product was purified using column chromatography (70 g silica gel, 9:1→1:1 hexane/EtOAc) to obtain 1.14 g of 1,3-bis(4-vinylbenzyloxy) propane (3.7 mmoles, 74%) in the form of a colorless oily substance. The analytical data for the product are shown below.

TLC $R_f$=0.40 (19:1 hexane/EtOAc); IR (film) ν 2859, 1630, 1510, 1404, 1364 cm$^{-1}$; $^1$H NMR (270 MHz, CDCl$_3$) δ 1.91 (t, J=6.2 Hz, 2H, CH$_2$CH$_2$O), 3.57 (t, J=6.2 Hz, 4H, CH$_2$CH$_2$O), 4.58 (s, 4H, $\overline{\text{Ar}}$CH$_2$), 5.23 (d, J=10.7 Hz, 2H, ArCH=$\overline{\text{CH}_2}$), 5.73 (d, J=17.7 Hz, 2H, ArCH=$\overline{\text{CH}_2}$), 6.70 (dd, J=10.7 Hz, 17.7 Hz, 2H, ArCH=$\overline{\text{CH}_2}$), 7.26 (m, 4H, ArH), 7.37 (m, 4H, ArH); $^{13}$C N$\overline{\text{MR}}$ (67.8 MHz, CDCl$_3$) δ 30.2 (CH$_2$), 67.3 (CH$_2$), 72.7 (CH$_2$), 113.6 (CH$_2$), 126.1 (CH), 127.8 (CH), 136.5 (CH), 136.8 (C), 138.1 (C); Anal. Calcd for C$_{21}$H$_{24}$O$_2$: C, 81.78; H, 7.84. Found: C, 81.61; H, 7.94.

Next, the monomer obtained above was used to synthesize high molecular weight ligands, and a metal complex catalyst of the present invention supported on a polymer was synthesized using a ligand exchange with a complex containing a metal having catalytic activity. The reaction is shown in FIG. 1.

Three freeze-pump-thaw operations were conducted under an argon atmosphere to de-gas 1 ml of a tert-butyl alcohol solution of 49.4 mg of N-4-[6-(4-vinylbenzyloxy)hexyl]oxyphthaloyl-(S)-tert-leucine (0.1 mmole), 194 mg of styrene (1.86 mmoles), 12.3 mg of 1,3-bis(4-vinylbenzyloxy) propane (0.04 mmole) and 3.2 mg of AIBN (0.02 mmole). The solution was subsequently agitated for sixty hours at 70° C. After the reaction solution was concentrated, 260 mg of a crude product was washed sequentially using 5 ml of dichloromethane and ethyl acetate (3×5 ml). The residue was dried under reduced pressure to obtain 123 mg of a polymer ligand (48%) in the form of a white powder. The analytical data for the product are shown below.

Anal. Calcd for C$_{950}$H$_{990}$N$_6$O$_{40}$: C, 86.89; H, 7.60; N, 0.64. Found: C, 86.99; H, 7.67; N, 0.69.

One milliliter of a chlorobenzene solution containing 31 mg of Rh$_2$(S-PTTL)$_4$ (22.4 μmoles) was added to 51.8 mg of the polymer ligand, and the reaction mixture was heated and allowed to reflux for nine hours. The supernatent solution was decanted, and the green residue was washed with a mixture of methanol and dichloromethane (1:1, 3×2 ml). The residue was subsequently dried under reduced pressure. One milliliter of chlorobenzene solution containing 31 mg of Rh$_2$(S-PTTL)$_4$ (22.4 μmoles) was added again, and the reaction mixture was heated and allowed to reflux for nine hours. Upon decantation of the supernatent solution, washing of the residue (1:1 mixture of methanol and dichloromethane, 3×2 ml) and drying under reduced pressure, 66 mg of a rhodium (II) complex supported on solids was obtained in the form of green powder. The analytical data for the product are shown below.

Anal. Calcd for C$_{1100}$H$_{1161}$N$_{15}$O$_{82}$Rh$_6$: C, 79.97; H, 7.08; N, 1.27; Rh, 3.74. Found: C, 79.61; H, 7.02; N, 1.28; Rh, 3.54.

The results indicated that 50% of the theoretical value of a two nuclei rhodium (II) complex was incorporated into the polymer ligands.

Example 2

A separate preparative method for a metal complex catalyst supported on a polymer is shown below.

[Chemical formula 15]

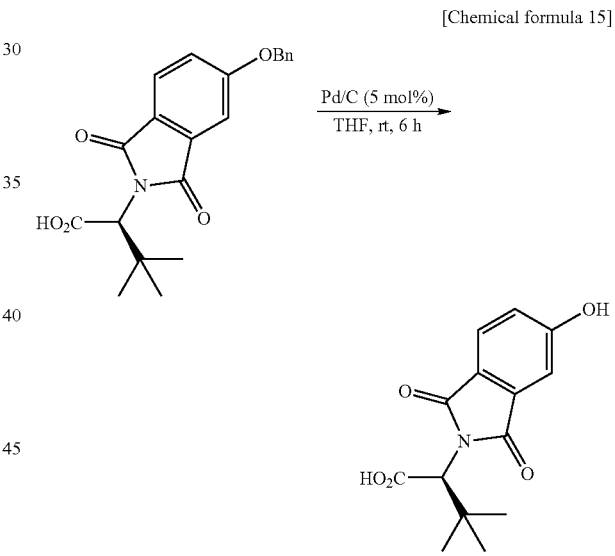

To 30 ml of a THF solution of 1.10 g of N-4-benzyloxyphthaloyl-(S)-tert-leucine (3.0 mmoles) was added 159 mg of 10% Pd/C, and the reaction mixture was agitated for six hours at room temperature in a hydrogen gas atmosphere. The reaction mixture was filtered, and the residue was washed using 10 ml of THF. The combined filtrate and washing was concentrated, and 810 mg of the crude product obtained was recrystallized from 5 ml of 3:1 hexane-ethyl acetate to obtain 665 mg of N-4-hydroyphthaloyl-(S)-tert-leucine (2.40 mmoles, 80%) in the form of colorless flaky crystals. The instrumental analysis data for the N-4-hydroxyphthaloyl-(S)-tert-leucine are shown below.

TLC $R_f$ 0.41 (9:1 CH$_2$Cl$_2$/MeOH); $^1$H NMR (400 MHz, CD$_3$OD) δ1.13 (s, 9H, C(CH$_3$)$_3$), 4.53 (s, 1H, CH(t-Bu) CO$_2$H), 7.11 (dd, J=2.2 Hz, J=8.2 Hz, 1H, Ar), 7.18 (d, J=2.2 Hz, 1H, Ar), 7.69 (d, dd, J=8.2 Hz, 1H, Ar); $^{13}$C NMR (100.4 MHz, CD$_3$OD) δ: 28.4 (CH$_3$), 36.3 (C), 60.6 (CH) 110.9

(CH), 121.7 (CH), 123.2 (C), 126.3 (CH), 135.5 (C), 165.0 (C), 169.4 (C), 169.4 (C), 170.9 (C); LRMS (FAB) m/z 278 (M+H); HRMS (FAB) calcd for $C_{14}H_{16}NO_5$: 278.1028. Found: 278.1029. Anal. Calcd for $C_{14}H_{15}NO_5$: C, 60.64; H, 5.45; N, 5.05. Found C, 60.79; H, 5.51; N, 5.03.

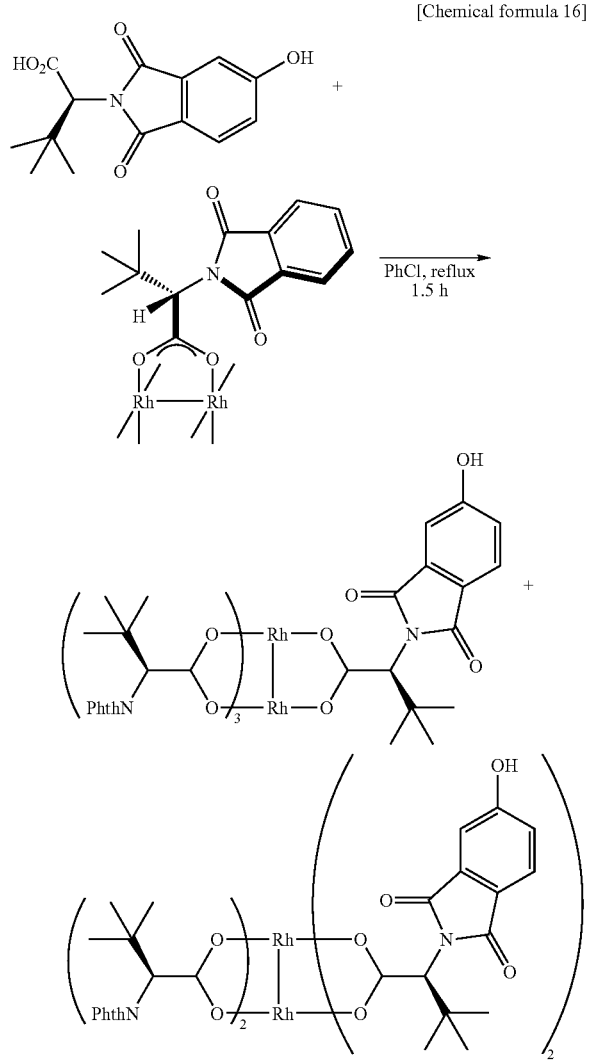

[Chemical formula 16]

Six milliliters of chlorobenzene was added to 568 mg of $Rh_2(S\text{-}PTTL)_4$ (0.4 mmoles) and 111 mg of 4-hydroxyphthaloyl-(S)-tert-leucine (0.4 mmole) under an argon atmosphere, and the mixture was heated and allowed to reflux for 1.5 hours. The reaction solution was allowed to cool and was subsequently diluted using 10 ml of ethyl acetate. The solution was washed using saturated aqueous sodium bicarbonate solution (2×10 ml), water (10 ml) and saturated aqueous saline solution (10 ml) and was subsequently dried using anhydrous sodium sulfate. The green crude product (581 mg) obtained upon filtration and concentration was purified using silica gel column chromatography (40 g silica gel, 4:1: 0.01=toluene:AcOEt:Et$_3$N), and 178 mg of green solids (31%) were obtained. The solids were dissolved in 0.5 ml of hot ethyl acetate and filtered. Green needle like crystals (150 mg, 0.10 mmole, 26%) of dirhodium(II) tris[N-phthaloyl-(S)-tert-leucinate][N-4-hydroxyphthaloyl-(S)-tert-leucinate]-bis(ethyl acetate) adduct were obtained when 1.5 ml of hexane was added to the filtrate and allowed to stand.

The data from the instrumental analysis of the product are shown below.

TLC R$_f$ 0.51 (1:2 hexane/AcOEt); mp>280° C.; $^1$H NMR (270 MHz, CDCl$_3$) δ 1.09 (s, 9H, C(CH$_3$)$_3$), 1.11 (br, 27H, C(CH$_3$)$_3$), 1.26 (t, J=7.26 Hz, 6H, CH$_3$CH$_2$), 2.05 (s, 6H, CH$_3$), 4.12 (q J=7.26 Hz, 4H, CH$_3$CH$_2$), 4.67 (s, 1H, CH(t-Bu)CO$_2$), 4.80 (br, 3H, CH(t-Bu)CO$_2$), 7.00 (m, 1H, Ar), 7.12 (m, 1H, Ar), 7.56-7.76 (m, 13H, Ar); $^{13}$C NMR (100.4 MHz, CDCl$_3$) δ 14.1 (CH$_3$), 21.0 (CH$_3$), 21.0 (CH$_3$), 28.0 (CH$_3$), 35.2 (C), 35.6, (C), 35.6 (C), 60.6 (CH$_2$), 61.3 (CH), 110.1 (CH), 120.3 (CH), 123.2 (CH), 124.8 (CH), 131.7 (C), 131.8 (C), 133.8 (CH), 167.5 (C), 171.8 (C), 185.6 (C), 186.7 (C), 187.0 (C); LRMS (FAB) m/z 1262 (M$^+$); HRMS (FAB) calcd for $C_{56}H_{56}N_4O_{17}Rh_2$: 1262.1751. Found: 1262.1753. Anal. Calcd for $C_{56}H_{56}N_4O_{17}Rh_2$-2AcOEt: C, 53.41; H, 5.04; N, 3.89. Found: C, 53.66; H, 5.21; N, 4.07.

[Chemical formula 17]

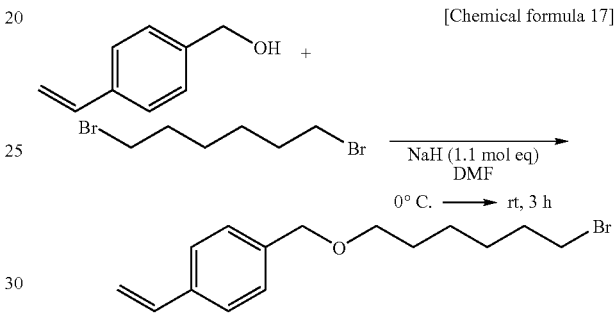

A DMF suspension (5 ml) of sodium hydride (50% in oil, 240 mg, 5.0 mmoles) was cooled to 0° C. under an argon atmosphere, and a DMF (1 ml) solution of 1.34 g of 4-vinylbenzyl alcohol (10 mmoles) was added. The reaction mixture was agitated for fifteen minutes, and a DMF solution (3 ml) of 3.66 g of 1,6-dibromohexane (15 mmoles) was added over at least five minutes. The reaction mixture was agitated at room temperature for three hours. Fifteen milliliters of water was added to the reaction solution while cooling using ice, and the solution was agitated for five minutes. The solution was extracted using ethyl acetate (2×40 ml). The combined organic layers were washed using 15 ml of saturated aqueous saline solution and dried using anhydrous sodium sulfate. Upon filtration and concentration, 4.11 g of the residue was purified using silica gel column chromatography (70 g silica gel, 20:1 hexane/Et$_2$O) and 1.72 g of 6-(4-vinylbenzyloxy) bromohexane (5.8 mmoles, 58%) was obtained in the form of an oily substance.

The data from the instrumental analysis of the product are shown below.

TLC R$_f$=0.53 (10:1 hexane/AcOEt); $^1$H NMR (270 MHz, CDCl$_3$) δ 1.37-1.48 (m, 4H, —(CH$_2$)—), 1.51-1.65 (m, 2H, —(CH$_2$)—), 1.81-1.91 (m, 2H, —(CH$_2$)—), 3.38-3.48 (m, 4H, OCH$_2$CH$_2$, BrCH$_2$CH$_2$), 4.49 (s, OCH$_2$Ar), 5.23 (d, J=10.9 Hz, 1H, ArCHCH$_2$), 5.74 (d, J=17.5 Hz, 1H, ArCHCH$_2$), 6.71 (dd, J=10.9 Hz, 17.5 Hz, 1H, ArCHCH$_2$), 7.28 (m, 2H, Ar), 7.39 (m, 2H, Ar); $^{13}$C NMR (100.4 MHz, CDCl$_3$) δ 25.4 (CH$_2$), 28.0 (CH$_2$), 29.6 (CH$_2$), 32.7 (CH$_2$), 33.8 (CH$_2$), 70.0 (CH$_2$), 72.5 (CH$_2$), 113.5 (CH$_2$), 126.0 (CH), 127.6 (CH), 136.4 (CH), 136.7 (C), 138.0 (C); MS (EI) m/1296 (M$^+$); HRMS (EI) m/z calcd for $C_{15}H_{21}BrO$: 296.0775. Found: 296.0778. Anal. Calcd for $C_{15}H_{21}BrO$: C, 60.61, H, 7.12, Br 26.88; found C, 60.79, H, 7.22, S 26.83.

[Chemical formula 18]

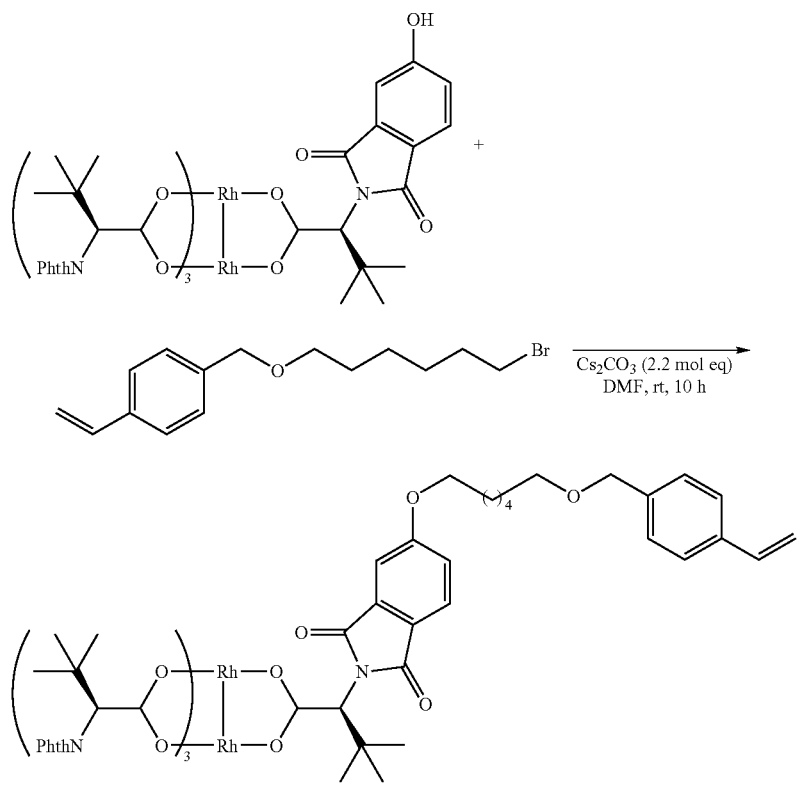

To a DMF solution (0.5 ml) of 57.6 mg of dirhodium (II) tris[N-phthaloyl-(S)-tert-leucinate][N-4-hydroxyphthaloyl-(S)-tert-leucinate]-bis(ethyl acetate) adduct (40 mmoles) was added 28.7 mg of $Cs_2CO_3$ (88 mmoles). The reaction solution was agitated for five minutes (the reaction solution gradually changed from blue green to yellow green). A DMF solution (0.5 ml) of 14.3 mg of 6-(4-vinylbenzyloxy) bromohexane (48 mmoles) was added, and the reaction solution was agitated for ten hours at room temperature. Two milliliters of water was added to the reaction solution, and the solution was extracted using ethyl acetate (2×5 ml). The combined organic layers were washed using saturated aqueous saline solution (2 ml) and dried using anhydrous sodium sulfate. The 67 mg of residue obtained upon filtration and concentration was purified using silica gel column chromatography (1 g silica gel, 3:1 n-hexane/AcOEt), and 60.7 mg of dirhodium (II) tris[N-phthaloyl-(S)-tert-leucinate]{N-4-[6-(4-vinylbenzyloxy)hexyloxy]-phthaloyl-(S)-tert-leucinate}-bis(ethyl acetate) adduct (36.8 mmoles, 92%) was obtained in the form of green flaky crystals.

The data from the instrumental analysis of the product are shown below.

TLC $R_f$ 0.54 (1:1 hexane/EtOAc); $^1$H NMR (270 MHz, $CDCl_3$) δ 1.02 (br, 36H, $C(CH_3)_3$), 1.18 (t, J=7.26 Hz, 6H, $CH_3CH_2$), 1.21, (m, 4H), 1.57 (m, 2H), 1.76 (m, 2H), 1.97 (s, 6H, $CH_3$), 3.40 (m, 2H), 4.00 (m, 2H), 4.12 (q J=7.26 Hz, 4H, $CH_3CH_2$), 4.40 (s, 2H), 4.64 (s, 1H, $CH(t-Bu)CO_2$), 4.70 (br, 3H, $CH(t-Bu)CO_2$), 5.16 (d, J=10.9 Hz, 1H, $ArCHCH_2$), 5.67 (d, J=16.9 Hz, 1H, $ArCHCH_2$), 6.71 (dd, J=10.9 Hz, 16.9 Hz, 1H, $ArCHCH_2$), 7.01 (m, 1H, Ar), 7.12 (m, 1H, Ar), 7.56-7.76 (m, 13H, Ar); LRMS (FAB) m/z 1478 ($M^+$); HRMS (FAB) calcd for $C_{71}H_{76}N_4O_{18}Rh_2$: 1478.3265. Found: 1478.3258.

Three freeze-pump-thaw operations were conducted under an argon atmosphere to de-gas 93 mg of a tert-butyl alcohol solution of 32.3 mg of styrene (0.31 mmoles), 2.1 mg of dirhodium (II) tris[N-phthaloyl-(S)-tert-leucinate][N-4-[6-(4-vinylbenzyloxy)hexyloxy]-phthaloyl-(S)-tert-leucinate]•bis (ethyl acetate) adduct (6.7 mmoles) and 0.54 mg of AIBN (3.2 mmoles). The solution was agitated for ten hours at 75° C. The residue (55.9 mg) obtained upon removing the solvent using distillation was placed on glass filter and washed sequentially using 2 ml of dichloromethane and ethyl acetate (3×1 ml). The residue was dried under reduced pressure to obtain 54.6 mg (88%) of a polymer ligand in the form of green powder. This reaction is shown in FIG. 2.

The data from the instrumental analysis for the product are shown below.

Anal. Calcd for $C_{1141}H_{1174}N_{20}O_{94}Rh_{10} \cdot 10AcOEt$: C, 76.34; H, 6.80; N, 1.51; Rh, 5.54. Anal: C, 76.80; H, 7.05; N, 1.50; Rh, 4.99.

Example 3

An intramolecular asymmetric C—H insertion reaction was conducted using the polymer supported metal complex catalyst obtained in Example 1. Toluene was added to an insoluble rhodium (II) catalyst, and the swollen catalyst was subsequently cooled to −78° C. A toluene solution of methyl 2-diazo-(6-phenyl) hexanoate, a reaction substrate, was added, and an intramolecular C—H insertion reaction proceeded. The supernatent solution was recovered upon completion of the reaction using decantation and was concentrated to yield a cyclic product. The residue was washed using ethyl acetate and the like and could be used again after drying it under reduced pressure.

The results are shown in the table below.

TABLE 1

Enantioselective C—H Insertion of α-Diazoester Catalyzed by (P)-S-TLRh₂(S-PTTL)₃

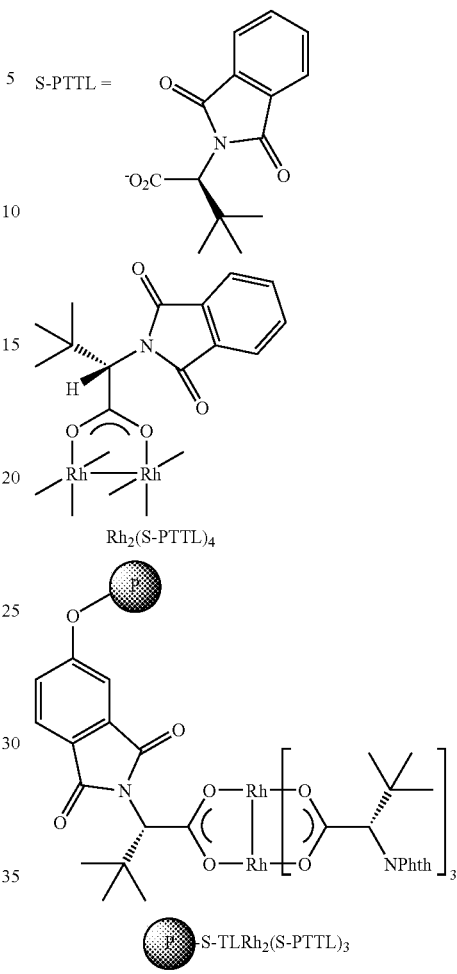

| entry | Rh(II) catalyst | cycle | time [h] | yield [%] (cis:trans:alkene) | cis ee [%] |
|---|---|---|---|---|---|
| 1[a] | Rh₂(S-PTTL)₄ | — | 0.5 | 85 (>99:—:—) | 95 |
| 2 | ●-S-TLRh₂(S-PTTL)₃ | 1 | 4 | 85 (>99:—:—) | 94 |
| 3 | ●-S-TLRh₂(S-PTTL)₃ | 2 | 4 | 82 (>99:—:—) | 94 |
| 4 | ●-S-TLRh₂(S-PTTL)₃ | 5 | 4 | 85 (>99:—:—) | 94 |
| 5 | ●-S-TLRh₂(S-PTTL)₃ | 10 | 4 | 81 (>99:—:—) | 94 |
| 6 | ●-S-TLRh₂(S-PTTL)₃ | 15 | 4 | 80 (>99:—:—) | 95 |
| 7 | ●-S-TLRh₂(S-PTTL)₃ | 20 | 4 | 83 (>99:—:—) | 94 |

[a]Adv. Synth. Catal. 2005, 347, 1483. 1 mol % of Rh₂(S-PTTL)₄ was used.
Note:

P-S-TL =

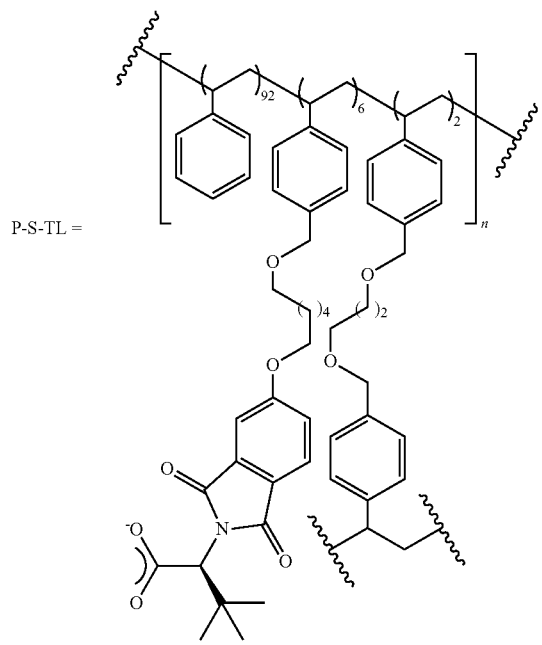

A reaction that uses a rhodium catalyst of the present invention may yield results comparable to those obtained when using Rh₂(S-PTTL)₄, a mother complex type homogeneous asymmetric catalyst that also exhibits chemical selectivity, diastereoselectivity and enantioselectivity while realizing asymmetric reactions at temperatures as low as −78° C., hitherto unobserved with solid supported transition metal complexes. In addition, the catalyst is insoluble in water, ethanol, ethyl acetate, acetone, ether, hexane, toluene, dichloromethane and the like making catalyst recovery and reaction product purification easy to conduct. In addition, recovered catalysts can be reutilized without losing their efficiency. For example, the yield in the reaction shown above (Chemical formula 7, $R^1$=hydrogen atom, $R^2$=methyl group) was 85%, the chemical selectivity for the C—H insertion/alkene formation was 99:1 and the asymmetric yield was 94%. After the reaction, the catalyst was repeatedly recovered and reutilized. The yield after recycling continuously twenty times was 83%, the chemical selectivity for C—H insertion/alkene formation was >99:1, the asymmetric yield was 94%, and almost no change was observed in yield and selectivity. The rhodium (II) catalyst of the present invention can be referred to as a catalyst that is extremely useful in asymmetric carbene reactions such as C—H insertion reactions and the like.

Example 4

The rhodium catalyst prepared in Example 1 was used to conduct an intramolecular asymmetric C—H insertion reaction. Toluene was added to the insoluble rhodium (II) catalyst to swell the catalyst, and the catalyst was subsequently cooled to −60° C. An intramolecular C—H insertion reaction proceeded when a toluene solution of methyl 2-(2-benzyloxyphenyl)-2-diazoacetate, the reaction substrate, was added. Upon conclusion of the reaction, the supernatent solution was recovered through decantation and concentrated to yield a cyclic product. The residue was washed using ethyl acetate and the like and dried under reduced pressure, and the catalyst could be utilized again.

The results are shown in the table below.

TABLE 2

Enantioselective C—H Insertion of Aryldiazoacetate Catalyzed by (P)-S-TLRh$_2$(S-PTTL)$_3$

| entry | Rh(II) catalyst | cycle | temp [° C.] | time [h] | yield [%] | ee [%] |
|---|---|---|---|---|---|---|
| 1[a] | Rh$_2$(S-PTTL)$_4$ | — | −78 | 1 | 86 | 94 |
| 2[a] | Rh$_2$(S-PTTL)$_4$ | — | −60 | 0.5 | 87 | 90 |
| 3 | (P)-S-TLRh$_2$(S-PTTL)$_3$ | 1 | −60 | 6 | 82 | 89 |
| 4 | (P)-S-TLRh$_2$(S-PTTL)$_3$ | 2 | −60 | 6 | 85 | 91 |
| 5 | (P)-S-TLRh$_2$(S-PTTL)$_3$ | 5 | −60 | 6 | 83 | 90 |
| 6 | (P)-S-TLRh$_2$(S-PTTL)$_3$ | 10 | −60 | 6 | 82 | 90 |
| 7 | (P)-S-TLRh$_2$(S-PTTL)$_3$ | 15 | −60 | 6 | 78 | 90 |

[a]Org. Lett. 2002, 4, 3887. 1 mol % of Rh$_2$(S-PTTL)$_4$ was used.

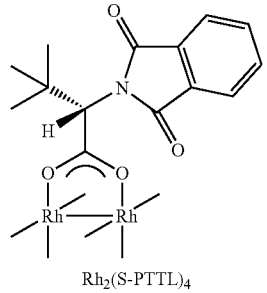

Rh$_2$(S-PTTL)$_4$

TABLE 2-continued

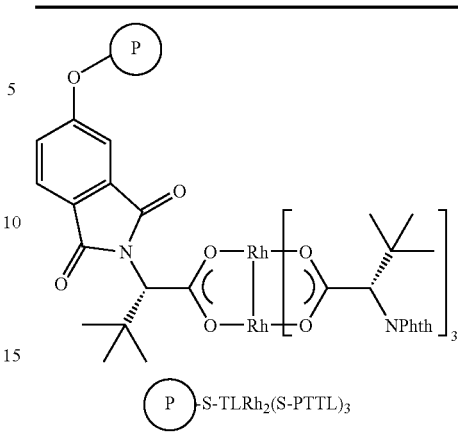

(P)-S-TLRh$_2$(S-PTTL)$_3$

Asymmetric reactions were realized at temperatures as low as −60° C. in reactions that used a rhodium catalyst of the present invention. The reactions yielded results comparable to those obtained when using Rh$_2$(S-PTTL)$_4$, a mother complex type homogeneous asymmetric catalyst, as far as chemical selectivity, diastereoselectivity and enantioselectivity were concerned. The yields, the locations and diastereoselectivity and asymmetric yields remained unchanged when the rhodium catalyst of the present invention was repeatedly recycled fifteen times. The rhodium (II) catalyst of the present invention can be referred to as a catalyst that is extremely useful for substrates having diverse structures such as those described above.

Example 5

[Chemical formula 19]

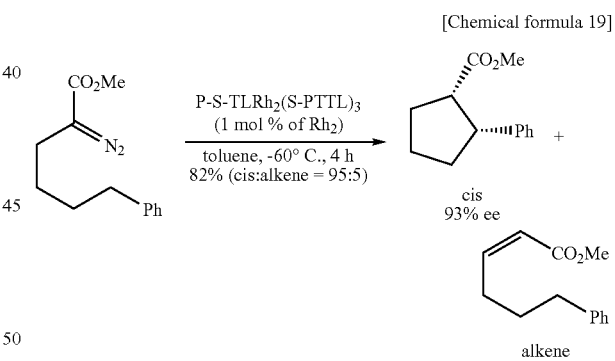

A reaction test tube containing 28.6 mg of a solid phase supported rhodium (II) complex and 1.0 ml of toluene was cooled to −78° C., 1.0 ml of a toluene solution containing 93.0 mg of methyl 2-diazo-(6-phenyl) hexanoate (0.40 mmole) was added, and the reaction mixture was agitated for four hours at the temperature. The supernatent solution was decanted, and the residue was washed sequentially using toluene (2×2 ml) and ethyl acetate (2 ml). The combined supernatent solution was concentrated, and 90 mg of the residue was subsequently purified using column chromatography (6 g of silica gel, 15:1 n-hexane/EtOAc). Methyl (1S, 2R)-2-phenylcyclopentane carboxylate (69.0 mg, 0.34 mmole, 85%) was obtained in the form of a colorless oily substance. The optical purity of the methyl (1S,2R)-2-phenylcyclopentane carboxylate in the mixture was found to be 94% ee according to HPLC analysis. The recovered solid phase supported rhodium (II) complex was used repeatedly for the same reaction after drying the complex under reduced pressure.

The analytical data for the methyl (1S,2R)-2-phenylcyclopentane carboxylate are shown below.

TLC $R_f$ 0.39 (5:1 hexane/EtOAc); IR (neat) ν 1732 (C=O), 1200, 1171, 700 cm$^{-1}$; $^1$H NMR (400 MHz, CDCl$_3$) δ 1.70 (m, 1H, CH$_2$), 1.95-2.15 (m, 5H, CH$_2$), 3.16 (ddd, J=6.2, 9.0, 9.0 Hz, 1H, C2-H), 3.22 (s, 3H, $\overline{CO_2CH_3}$), 3.41 (ddd, J=7.1, 9.0, 9.0 Hz, 1H, $\overline{C_1}$-H), 7.15-7.28 (m, 5H, ArH); $^{13}$C NMR (100 MHz, CDCl$_3$) δ $\overline{24}$.8 (CH$_2$), 28.6 (CH$_2$), 3$\overline{1}$.2 (CH$_2$), 49.2 (CH), 49.8 (CH), 50.9 (CH$_3$), 126.3 (CH), 127.8 (CH), 127.9 (CH), 141.5 (C), 174.9 (C=O); LRMS (EI) m/z 204 (M$^+$); HRMS (EI) calcd for C$_{13}$H$_{16}$O$_2$ (M$^+$) 204.1150. Found: 204.1151; Anal. Calcd for C$_{13}$H$_{16}$O$_2$: C, 76.44; H, 7.90. Found: C, 76.33; H, 7.98.

The enantiomeric excess ratio (ee) was determined to be 94 ee according to the HPLC analysis using a chiral column. Analytical conditions: column Daicel Chiralcel OJ-H followed by Daicel Chiralpak AS-H; eluent: 100:1 hexane/i-PrOH; 1.0 mL/min; detection: 254 nm; retention time: 12.9 min for (1R,2S) enantiomer (minor), 14.7 min for (1S,2R) enantiomer (major).

Example 6

[Chemical formula 20]

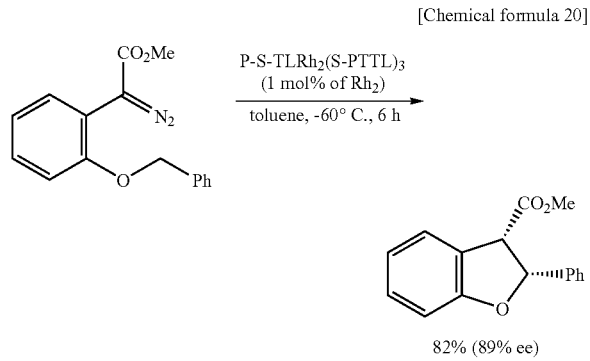

82% (89% ee)

A reaction test tube containing 28.6 mg of a solid phase supported rhodium (II) complex and 1.0 ml of toluene was cooled to −60° C., 1.0 ml of a toluene solution of 113 mg of methyl 2-(2-benxyloxyphenyl)-2-diazoacetate (0.40 mmole) was added, and the reaction mixture was agitated for six hours at the temperature. The supernatent solution was decanted, and the residue was washed sequentially using toluene (2×2 ml) and ethyl acetate (2 ml). The combined supernatent solution was concentrated, and 90 mg of the residue was subsequently purified using column chromatography (6 g of silica gel, 15:1 n-hexane/EtOAc). Methyl (2R,3S)-2,3-cis-2,3-dihydro-2-phenylbenzofuran-3-carboxylate (67.0 mg, 0.33 mmole, 82%) was obtained in the form of colorless needle-like crystals. The recovered solid phase supported rhodium (II) complex was used repeatedly for the same reaction after drying the complex under reduced pressure.

The analytical data for the methyl (2R,3S)-2,3-cis-2,3-dihydro-2-phenylbenzofuran-3-carboxylate are shown below.

TLC $R_f$ 0.35 (5:1 hexane/EtOAc); mp 91-92° C.; IR (neat) ν 1736 (C=O), 1480, 1229, 1213 cm$^{-1}$; $^1$H NMR (270 MHz, CDCl$_3$) δ 3.21 (s, 3H, CO$_2$CH$_3$), 4.62 (d, J=9.9 Hz, 1H, CH CO$_2$CH$_3$), 5.99 (d, J=9.9 Hz, 1H, OCHPh), 6.01-6.98 (m, 2H, ArH), 7.22-7.38 (m, 2H, ArH); $^{13}$C NMR (67.8 MHz, CDCl$_3$) δ 5$\overline{1}$.5 (CH$_3$), 53.9 (CH), 8$\overline{5}$.6 (CH), 109.9 (CH), 121.2 (CH), 124.7 (C), 125.8 (CH), 126.1 (CH), 128.1 (CH), 128.2 (CH), 129.5 (CH), 137.0 (C), 160.4 (C), 170.2 (C=O); LRMS (EI) m/z 254 (M$^+$); HRMS (EI) calcd for C$_{16}$H$_{14}$O$_3$ (M$^+$) 254.0943. Found: 254.0946; Anal. Calcd for C$_{16}$H$_{14}$O$_3$: C, 75.57; H, 5.55. Found: C, 75.38; H, 5.77.

The enantiomeric excess ratio (ee) was determined to be 89% ee according to an HPLC analysis using a chiral column. Analytical conditions: column Daicel Chiralcel OD-H; eluent: 9:1 hexane/iPrOH; 1.0 mL/min; detection: 254 nm; retention time: 7.9 min for (2R,3S) enantiomer (major), 14.1 min for (2S,3R) enantiomer (minoir).

Example 7

The recyclability of the catalyst of the invention in an intramolecular aromatic ring C—H insertion reaction was investigated in the present example. The catalyst of the invention was insoluble and could be removed from a reaction mixture using filtration upon conclusion of the reaction. After filtration the collected catalyst was washed several times using an appropriate organic solvent, and it could be utilized again after the solvent was removed using distillation under reduced pressure. No decline in reactivity and asymmetry identification capability was observed in the present example after the solid phase supported metal catalyst of the present invention was used repeatedly for one hundred times as described below.

To a reaction test tube containing 7.4 mg of the solid phase supported rhodium (II) complex (2 mole % of the catalyst) obtained in Example 1 and 0.5 ml of methyl dichloromethane was added 0.5 ml of a dichloromethane solution containing 30.8 mg of methyl 2-diazo-4,4-diphenyl-3-oxopentanoate at room temperature. The reaction mixture was agitated for twenty minutes at the temperature. The supernatent solution was decanted, and the residue was subsequently washed using 1 ml of dichloromethane. The supernatent solution and washing were combined and concentrated to give 28 mg of a residue that was purified using column chromatography (1 g of silica gel, benzene) to obtain 24.1 mg of methyl (3S)-3-methyl-3-phenyl-2-oxoindane-1-carboxylate (86%) in the form of pale blue solids. The optical purity of the methyl (3S)-3-methyl-3-phenyl-2-oxyindane-1-carboxylate in the mixture was found to be 91% ee according to HPLC analysis. The recovered solid phase supported rhodium (II) complex was dried under reduced pressure and used repeatedly for the same reaction.

The analytical data for the methyl (3S)-3-methyl-3-phenyl-2-oxyindane-1-carboxylate are shown below.

TLC $R_f$ 0.55 (2:1 hexane/EtOAc); mp 81.0-82.0° C.; IR (KBr) ν 2971, 2949, 1595, 1475, 1440 cm$^{-1}$; $^1$H NMR (270 MHz, CDCl$_3$, almost enol form) δ 1.80 (3H, s, CH$_3$), 3.98 (3H, s, CO$_2$CH$_3$), 7.07-7.13 (2H, m, ArH), 7.20-7.3$\overline{2}$ (6H, m, ArH), 7.65 (1$\overline{H}$, d, J=7.3 Hz, ArH), 11.0$\overline{0}$ (1H, brs, enol-OH); $^{13}\overline{C}$ NMR (67.8 MHz, CDCl$_3$) δ $\overline{2}$1.7 (CH$_3$), 51.6 (CH$_3$), 54.8 (C), 102.3 (C), 120.5 (CH), 122.8 (CH), 124.5 (CH), 126.6 (CH), 127.3 (CH), 127.4 (CH), 128.5 (CH), 137.5 (C), 140.2 (C), 145.0 (C), 169.5 (C), 186.2 (C); LRMS (EI) m/z 280 (M$^+$), 248, 233, 219, 205, 192; HRMS (EI) calcd for C$_{18}$H$_{16}$O$_3$ (M$^+$) 280.1099. Found: 280.1092; Anal. Calcd for C$_{18}$H$_{16}$O$_3$: C, 77.12; H, 5.75. Found: C, 77.33; H, 5.92.

The results are show in the table below.

TABLE 3

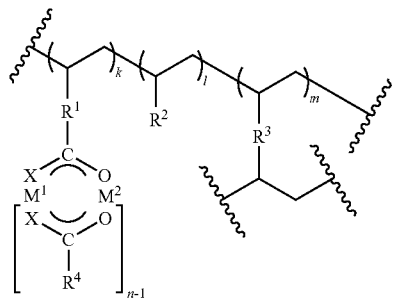

| entry | Rh(II) catalyst | cycle | time [min] | yield [%] | ee$^a$ [%] |
|---|---|---|---|---|---|
| 1$^b$ | Rh$_2$(S-PTTL)$_4$ | — | 5 | 90 | 90 |
| 2 | (P)-S-TLRh$_2$(S-PTTL)$_3$ | 1 | 20 | 86 | 91 |
| 3 | (P)-S-TLRh$_2$(S-PTTL)$_3$ | 10 | 20 | 90 | 91 |
| 4 | (P)-S-TLRh$_2$(S-PTTL)$_3$ | 50 | 20 | 90 | 91 |
| 5 | (P)-S-TLRh$_2$(S-PTTL)$_3$ | 100 | 20 | 88 | 92 |

$^a$Determined by HPLC analysis after demethoxycarbonylation.
$^b$Tsutsui, H.; Yamaguchi, Y.; Kitagaki, S.; Nakamura, S.; Anada, M.; Hashimoto, S. Tetrahedron Asymmetry 2003, 14, 817-821.

Next, 0.5 ml of an aqueous dimethyl sulfoxide solution (1:9 water:DMSO) containing 24.1 mg of (3S)-3-methyl-3-phenyl-2-oxyindane-1-carboxylate (0.086 mmole) obtained from the reaction described above was agitated for thirty minutes at 120° C. The reaction solution changed to pale orange. The solution was allowed to cool, 5 ml of water was added, and the solution was extracted using 20 ml of ethyl acetate. The organic layer was washed using 5 ml of saturated aqueous saline solution and was dried using anhydrous sodium sulfate. The solvent was removed by distillation under reduced pressure, and the residue obtained was purified using silica gel column chromatography (1 g, 1:2 hexane/benzene) to obtain 18.2 mg of (S)-3-methyl-3-phenyl-2-indanone (95%) in the form of a pale orange oily material.

The analytical data for (S)-3-methyl-3-phenyl-2-indanone are shown below.

TLC R$_f$ 0.65 (2:1 hexane/EtOAc); IR (film) ν 3025, 2971, 1752, 1597, 1495, 1480 cm$^{-1}$; $^1$H NMR (270 MHz, CDCl$_3$) δ 1.76 (3H, s, CH$_3$), 3.53 (1H, d, J=21.8 Hz, CH$_2$), 3.68 (1H, d, J=21.8 Hz, CH$_2$), 7.16-7.41 (9H, m, ArH); $^{13}$C NMR (67.8 MHz, CDCl$_3$) δ 23.8 (CH$_3$), 41.6 (CH$_2$), 58.3 (C), 124.8 (CH), 125.2 (CH), 126.7 (CH), 126.9 (CH), 127.7 (CH), 127.9 (CH), 128.4 (CH), 135.8 (C), 142.0 (C), 146.4 (C), 216.1 (C); LRMS (EI) m/z 222 (M$^+$), 194, 179, 165, 152; HRMS (EI) calcd for C$_{16}$H$_{14}$O (M$^+$) 222.1045, found 222.1046; Anal. Calcd for C$_{16}$H$_{14}$O: C, 86.45; H, 6.35. Found: C, 86.40; H, 6.40.

The enantiomeric excess ratio (ee) was determined to be 97% ee according to an HPLC analysis using a chiral column. Analytical conditions: column: Daicel Chiralcel OD-H; eluent: 200:1 hexane/2-propanol; flow: 1.0 mL/min; detection: 254 nm; retention time: 9.4 min (major enantiomer 5), 10.8 min (minor enantiomer R).

What is claimed is:

1. A polymer-supported metal complex catalyst represented by the following chemical formula 1

[chemical formula 1]

$$\left[\begin{array}{c} \cdots \left(\begin{array}{c} R^1 \\ | \\ C \\ | \\ X \diagdown \diagup O \\ M^1 \quad M^2 \\ X \diagup \diagdown O \\ | \\ C \\ | \\ R^4 \end{array}\right)_k \left(\begin{array}{c} R^2 \\ \end{array}\right)_l \left(\begin{array}{c} R^3 \\ \end{array}\right)_m \cdots \end{array}\right]_{n-1}$$

wherein M$^1$ and M$^2$, which may be identical to or different from the others, are selected from a group consisting of rhodium, palladium, ruthenium, rhenium, iron, nickel, copper, platinum, bismuth, cobalt, chromium, molybdenum, and tungsten; X is an oxygen atom; R$^4$ is an alkyl group, an aryl group, an aralkyl group, an alkyloxy group or an alkylamino group, which may have substituents; k is 1 to 15% and m is more than 0 and equal to or less than 99% based on k+l+m and l is the remainder; and n is an integer between 2 and 4, which is determined by the valences of M$^1$ and M$^2$; and R$^1$ to R$^3$ are defined below, wherein the polymer-supported metal complex catalyst is prepared by a method comprising the steps of:

(1) performing a ligand exchange reaction between a coordinating compound and a complex, wherein the coordinating compound is represented by the chemical formula 21:

[chemical formula 21]

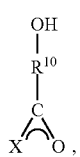

wherein R$^{10}$ is a divalent hydrocarbon group, which may contain heteroatoms; and X is defined as above, and the complex is represented by the following chemical formula 5 so that metals (M$^1$ and M$^2$) are supported by the coordinating monomer, (R$^4$CXO)$_n$M$^1$M$^2$,     [chemical formula 5]

wherein R$^4$, X, n, M$^1$ and M$^2$ are defined as above;

(2) separating a compound represented by the following chemical formula 22 from the coordinating compound with supporting metals (M$^1$ and M$^2$),

[chemical formula 22]

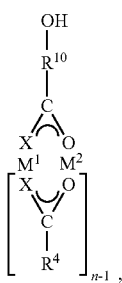

wherein $R^{10}$, $R^4$, X, n, $M^1$ and $M^2$ are defined as above;

(3) preparing (a) a coordinating monomer represented by the following chemical formula 23 by introducing a vinyl group to the coordinating compound

[chemical formula 23]

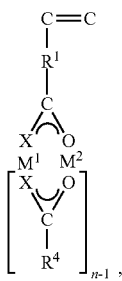

wherein $R^1$ is a divalent hydrocarbon group, which may contain heteroatoms, and $R^4$, X, n, $M^1$ and $M^2$ are defined as above; and (4) copolymerizing (a) the coordinating monomer with supporting metals ($M^1$ and $M^2$), (b) a hydrophobic monomer represented by the chemical formula 3,

[chemical formula 3]

wherein $R^2$ is an aromatic group and other carbons in the vinyl group may have substituents, and (c) a polymeric monomer represented by the chemical formula 4

[chemical formula 4]

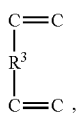

wherein $R^3$ is a divalent hydrocarbon group represented by the chemical formula

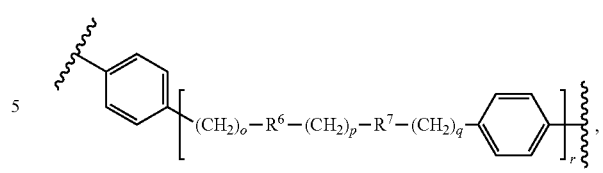

wherein $R^6$ and $R^7$ are independently —O—, —S—, —$NR^8$— or $PR^9$—, wherein $R^8$ and $R^9$ are independently a hydrogen atom, an alkyl group or an aryl group; o is an integer between 0 and 4; p is an integer between 1 and 12; q is an integer between 0 and 4; and r is 1 or 2.

2. A method for manufacturing a polymer-supported metal complex catalyst represented by the following chemical formula 1,

[chemical formula 1]

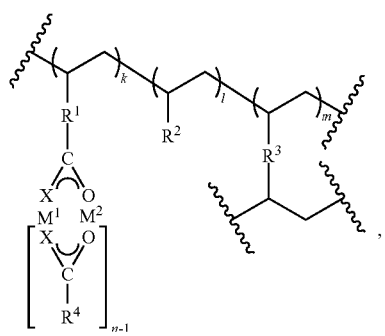

wherein $M^1$ and $M^2$, which may be identical to or different from the others, are selected from a group consisting of rhodium, palladium, ruthenium, rhenium, iron, nickel, copper, platinum, bismuth, cobalt, chromium, molybdenum, and tungsten; X is an oxygen atom; $R^4$ is an alkyl group, an aryl group, an aralkyl group, an alkyloxy group or an alkylamino group, which may have substituents; k is 1 to 15% and m is more than 0 and equal to or less than 99% based on k+l+m and l is the remainder; and n is an integer between 2 and 4, which is determined by the valences of $M^1$ and $M^2$; and $R^1$ to $R^3$ are defined below, comprising the steps of:

(1) performing a ligand exchange reaction between a coordinating compound and a complex, wherein the coordinating compound is represented by the chemical formula 21:

[chemical formula 21]

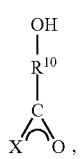

wherein $R^{10}$ is a divalent hydrocarbon group, which may contain heteroatoms; and X is defined as above, and the complex is represented by the following chemical formula 5 so that metals ($M^1$ and $M^2$) are supported by the coordinating monomer, $(R^4CXO)_nM^1M^2$     [chemical formula 5]

wherein $R^4$, X, n, $M^1$ and $M^2$ are defined as above;

(2) separating a compound represented by the following chemical formula 22 from the coordinating compound with supporting metals ($M^1$ and $M^2$),

[chemical formula 22]

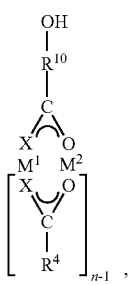

wherein $R^{10}$, $R^4$, X, n, $M^1$ and $M^2$ are defined as above;

(3) preparing (a) a coordinating monomer represented by the following chemical formula 23 by introducing a vinyl group to the coordinating compound

[chemical formula 23]

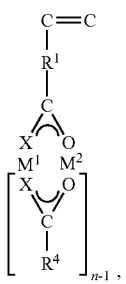

wherein $R^1$ is a divalent hydrocarbon group, which may contain heteroatoms, and $R^4$, X, n, $M^1$ and $M^2$ are defined as above; and (4) copolymerizing (a) the coordinating monomer with supporting metals ($M^1$ and $M^2$),
(b) a hydrophobic monomer represented by the chemical formula 3,

[chemical formula 3]

wherein $R^2$ is an aromatic group and other carbons in the vinyl group may have substituents, and (c) a polymeric monomer represented by the chemical formula 4

[chemical formula 4]

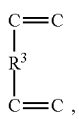

wherein $R^3$ is a divalent hydrocarbon group represented by the chemical formula

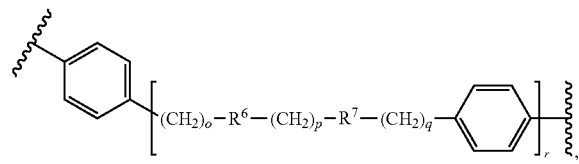

wherein $R^6$ and $R^7$ are independently —O—, —S—, —$NR^8$— or $PR^9$—, wherein $R^8$ and $R^9$ are independently a hydrogen atom, an alkyl group or an aryl group;

o is an integer between 0 and 4; p is an integer between 1 and 12; q is an integer between 0 and 4; and r is 1 or 2.

3. A polymer-supported metal complex catalyst of chemical formula 1:

[chemical formula 1]

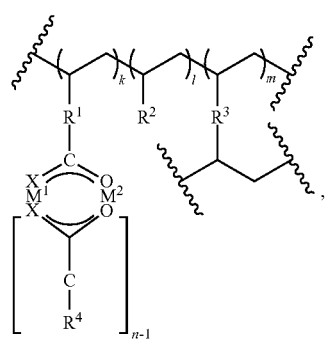

wherein, $M^1$ and $M^2$, which may be identical to or different from the others, are selected from a group consisting of rhodium, palladium, ruthenium, rhenium, iron, nickel, copper, platinum, bismuth, cobalt, chromium, molybdenum, and tungsten; and X is an oxygen atom, a sulfur atom or a group represented by =$NR^5$, wherein $R^5$ represents a hydrogen atom or an alkyl group, and $R^4$ is an alkyl group, an aryl group, an aralkyl group, an alkyloxy group or an alkylamino group, which may have substituents; k is 1 to 15% and m is more than 0 and equal to or less than 99% based on k+l+m and l is the remainder; and n is an integer between 2 and 4, which is determined by the valences of $M^1$ and $M^2$; $R^1$ has the formula:

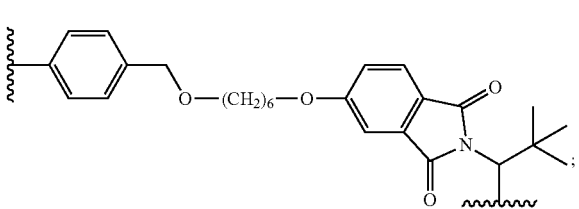

$R^2$ is phenyl; and
$R^3$ has the formula:

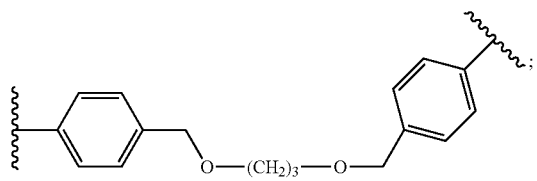

wherein the polymer-supported metal complex catalyst is prepared by a method comprising the steps of:
(1) performing a copolymerization reaction of N-4-[6-(4-vinylbenzyloxy)-hexyl]oxy-phthaloyl-(S)-tert-leucine, styrene, and 1,3-bis(4-vinylbenzyloxy)propane to provide a crosslinked polymer; and
(2) performing a ligand exchange reaction between the crosslinked polymer and a complex of chemical formula 5:

$(R^4CXO)_nM^1M^2$     [chemical formula 5]

wherein, $R^4$, X, n, $M^1$ and $M^2$ are defined as above.

4. A polymer-supported metal complex catalyst of chemical formula 1:

[chemical formula 1]

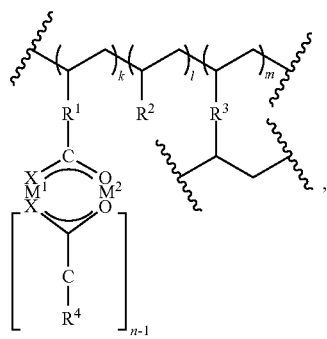

wherein, $M^1$ and $M^2$, which may be identical to or different from the others, are selected from a group consisting of rhodium, palladium, ruthenium, rhenium, iron, nickel, copper, platinum, bismuth, cobalt, chromium, molybdenum, and tungsten; and X is an oxygen atom, a sulfur atom or a group represented by $=NR^5$, wherein $R^5$ represents a hydrogen atom or an alkyl group, and $R^4$ is an alkyl group, an aryl group, an aralkyl group, an alkyloxy group or an alkylamino group, which may have substituents; k is 1 to 15% and m is more than 0 and equal to or less than 99% based on k+l+m and l is the remainder; and n is an integer between 2 and 4, which is determined by the valences of $M^1$ and $M^2$; $R^1$ has the formula:

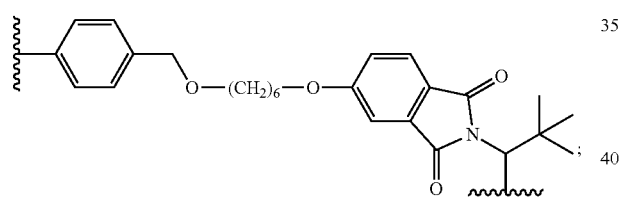

$R^2$ is phenyl; and
$R^3$ has the formula:

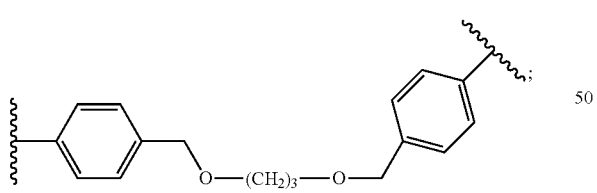

wherein the polymer-supported metal complex catalyst is prepared by a method comprising the steps of:
(1) performing a ligand exchange reaction between a coordinating compound, wherein the coordinating compound is 4-hydroxyphthaloyl-(S)-tert-leucine, and a complex of chemical formula 5:

$(R^4CXO)_nM^1M^2$      [chemical formula 5], wherein, $R^4$, X, n, $M^1$ and $M^2$ are defined as above;
(2) separating a compound having the formula $[R^4CXO]_{n-1}$[4-hydroxyphthaloyl-(S)-tert-leucine]$M^1M^2$ from products of the ligand exchange reaction;

(3) introducing a vinyl group into the coordinating compound to provide a compound having the formula $[R^4CXO]_{n-1}$[N-4-{6-(4-vinylbenzyloxy)hexyl}oxyphthaloyl-(S)-tert-leucine]$M^1M^2$; and
(4) copolymerizing the compound from (3) with styrene and 1,3-bis(4-vinylbenzyloxy)propane.

5. A method for using the catalyst of claim 3 or 4 in a reaction that is selected from the group consisting of a C—H insertion reaction; cyclopropanization reaction; X—H insertion reaction (wherein X is silica, oxygen, sulfur, or nitrogen); [2,3]-sigmatropy-rearrangement reaction of oxoniumylide, sulfoniumylide or ammoniumylide; [1,2]-rearrangement reaction of oxoniumylide, sulfoniumylide or ammoniumylide; 1,3-dipolar cycloaddition reaction of carbonylylide, thiocarbonylylide or azomethineylide; hydrogenation, hydrosilanization, hydroformylation or silylformylation reaction of alkene or alkyne; hydrosilanization reaction of α,β-unsaturated carbonyl compound; Mukouyama-aldol reaction of silylenolether or silylketeneacetal with aldehyde; carbonilene reaction; or Diels-Alder reaction.

6. A method for manufacturing a polymer-supported metal complex catalyst of chemical formula 1:

[chemical formula 1]

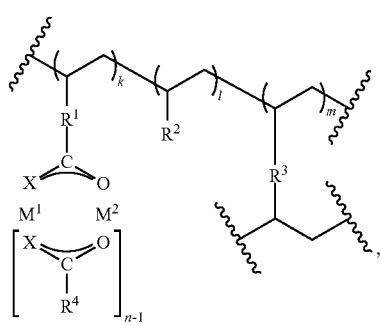

wherein, $M^1$ and $M^2$, which may be identical to or different from the others, are selected from a group consisting of rhodium, palladium, ruthenium, rhenium, iron, nickel, copper, platinum, bismuth, cobalt, chromium, molybdenum, and tungsten; and X is an oxygen atom, a sulfur atom or a group represented by $=NR^5$, wherein $R^5$ represents a hydrogen atom or an alkyl group, and $R^4$ is an alkyl group, an aryl group, an aralkyl group, an alkyloxy group or an alkylamino group, which may have substituents; k is 1 to 15% and m is more than 0 and equal to or less than 99% based on k+l+m and l is the remainder; and n is an integer between 2 and 4, which is determined by the valences of $M^1$ and $M^2$; $R^1$ has the formula:

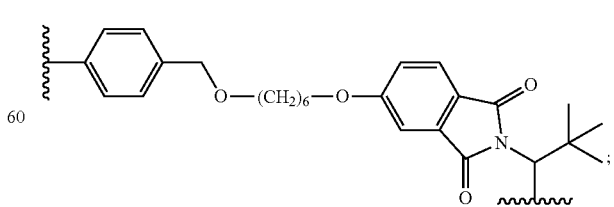

$R^2$ is phenyl; and
$R^3$ has the formula:

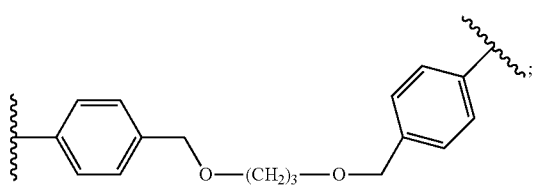

the method comprising:
(1) copolymerizing N-4-[6-(4-vinylbenzyloxy)hexyl]oxyphthaloyl-(S)-tert-leucine, styrene, and 1,3-bis(4-vinylbenzyloxy)propane to form a crosslinked polymer; and
(2) performing a ligand exchange reaction between the crosslinked polymer and a complex of chemical formula 5:

$(R^4CXO)_nM^1M^2$  [chemical formula 5], wherein $R^4$, X, n, $M^1$ and $M^2$ are defined as above.

7. A method for manufacturing a polymer-supported metal complex catalyst of chemical formula 1:

[chemical formula 1]

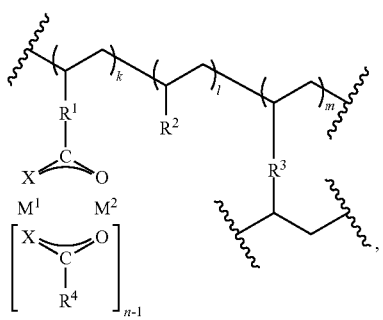

wherein, $M^1$ and $M^2$, which may be identical to or different from the others, are selected from a group consisting of rhodium, palladium, ruthenium, rhenium, iron, nickel, copper, platinum, bismuth, cobalt, chromium, molybdenum, and tungsten; and X is an oxygen atom, a sulfur atom or a group represented by $=NR^5$, wherein $R^5$ represents a hydrogen atom or an alkyl group, and $R^4$ is an alkyl group, an aryl group, an aralkyl group, an alkyloxy group or an alkylamino group, which may have substituents; k is 1 to 15% and m is more than 0 and equal to or less than 99% based on k+l+m and l is the remainder; and n is an integer between 2 and 4, which is determined by the valences of $M^1$ and $M^2$; $R^1$ has the formula:

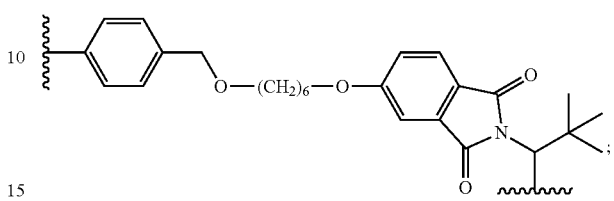

$R^2$ is phenyl; and
$R^3$ has the formula:

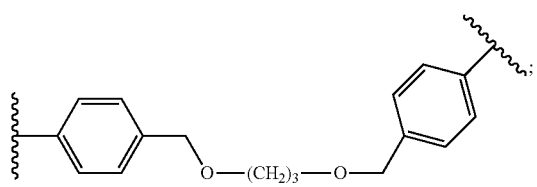

the method comprising:
(1) performing a ligand exchange reaction between a coordinating compound, wherein the coordinating compound is 4-hydroxyphthaloyl-(S)-tert-leucine, and a complex of chemical formula 5:

$(R^4CXO)_nM^1M^2$  [chemical formula 5], wherein, $R^4$, X, n, $M^1$ and $M^2$ are defined as above;
(2) separating a compound having the formula $[R^4CXO]_{n-1}$[4-hydroxyphthaloyl-(S)-tert-leucine]$M^1M^2$ from products of the ligand exchange reaction;
(3) introducing a vinyl group into the coordinating compound to provide a compound having the formula $[R^4CXO]_{n-1}$[N-4-{6-(4-vinylbenzyloxy)hexyl}oxyphthaloyl-(S)-tert-leucine]$M^1M^2$; and
(4) copolymerizing the compound from (3) with styrene and 1,3-bis(4-vinylbenzyloxy)propane.

* * * * *